(12) United States Patent
Zavros et al.

(10) Patent No.: US 12,270,054 B2
(45) Date of Patent: Apr. 8, 2025

(54) AUTOLOGOUS TUMOR ORGANOID AND IMMUNE CELL CO-CULTURES AND METHODS OF USE AS PREDICTIVE MODELS FOR PANCREATIC CANCER TREATMENT

(71) Applicant: University of Cincinnati, Cincinnati, OH (US)

(72) Inventors: Yana Zavros, Cincinnati, OH (US); Loryn Holokai, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 784 days.

(21) Appl. No.: 17/424,661

(22) PCT Filed: Jan. 24, 2020

(86) PCT No.: PCT/US2020/014925
§ 371 (c)(1),
(2) Date: Jul. 21, 2021

(87) PCT Pub. No.: WO2020/154579
PCT Pub. Date: Jul. 30, 2020

(65) Prior Publication Data
US 2022/0081679 A1 Mar. 17, 2022

Related U.S. Application Data

(60) Provisional application No. 62/796,307, filed on Jan. 24, 2019.

(51) Int. Cl.
*C12N 9/00* (2006.01)
*A61K 39/395* (2006.01)
(Continued)

(52) U.S. Cl.
CPC ........ *C12N 5/0693* (2013.01); *A61K 39/3955* (2013.01); *A61K 45/06* (2013.01);
(Continued)

(58) Field of Classification Search
CPC .................................................... C12N 5/0693
See application file for complete search history.

(56) References Cited

U.S. PATENT DOCUMENTS

| | | |
|---|---|---|
| 2017/0285003 A1 | 10/2017 | Hamilton et al. |
| 2018/0119107 A1 | 5/2018 | Neal et al. |
| 2018/0200379 A1 | 7/2018 | Sherman et al. |

FOREIGN PATENT DOCUMENTS

| | | | |
|---|---|---|---|
| WO | WO-2016113572 A1 * | 7/2016 | ........... A61K 31/337 |
| WO | 2017201502 A1 | 11/2017 | |

OTHER PUBLICATIONS

International Search Report mailed May 20, 2020 in reference to co-pending PCT/US2020/014925 filed Jan. 24, 2020.
(Continued)

*Primary Examiner* — Rosanne Kosson
(74) *Attorney, Agent, or Firm* — Dinsmore & Shohl LLP

(57) ABSTRACT

A method for preparing an autologous pancreatic tumor organoid and immune cell co-culture is provided, including: culturing pancreatic tumor cells obtained from a patient in a culture medium to provide a pancreatic tumor organoid and an organoid-conditioned medium; pulsing dendritic cells derived from the patient with a portion of the organoid-conditioned medium; contacting the pulsed dendritic cells with cytotoxic T lymphocytes (CTLs) obtained from the patient in the organoid-conditioned medium to activate the CTLs; isolating the activated CTLs; and co-culturing the pancreatic tumor organoid with the activated CTLs and myeloid derived suppressor cells (MDSCs) derived from the patient, to obtain an autologous pancreatic tumor organoid and immune cell co-culture that mimics the patient's pan-
(Continued)

creatic tumor microenvironment. Also provided are co-cultures obtained by the disclosed methods and methods of screening and determining whether a patient is likely to benefit from a candidate therapy.

10 Claims, 33 Drawing Sheets

(51) Int. Cl.
    *A61K 45/06*     (2006.01)
    *A61P 35/00*     (2006.01)
    *C12N 5/09*     (2010.01)
    *G01N 33/50*     (2006.01)

(52) U.S. Cl.
    CPC .......... *A61P 35/00* (2018.01); *G01N 33/5011* (2013.01); *C12N 2502/1114* (2013.01); *C12N 2503/02* (2013.01); *C12N 2503/04* (2013.01); *C12N 2533/90* (2013.01)

(56) References Cited

OTHER PUBLICATIONS

Chakrabarti, et al., "Mouse-Derived Gastric Organoid and Immune Cell Co-culture for the Study of the Tumor", Epithelial Cell Culture, Methods in Molecular Biology, vol. 1817, pp. 157-168, Jun. 30, 2018.
Gabrilovich, et al., "Myeloid-derived suppressor cells as regulators of the immune system", Nature Reviews Immunology, vol. 9, pp. 162-174, Mar. 1, 2009.
Holokai, et al., "Chemotherapy Induces Pancreatic Cancer Organoid Immune Evasion by Upregulating Programmed Death Ligand 1", FASEB Journal, vol. 32, Issue 1_supplement, p. 1, Apr. 20, 2018.
Tsai, et al., "Development of primary human pancreatic cancer organoids, matched stromal and immune cells and 3D tumor microenvironment models", BMC Cancer, vol. 18, Issue 335, pp. 1-13, Mar. 27, 2018.
Written Opinion mailed May 20, 2020 in reference to co-pending PCT/US2020/014925 filed Jan. 24, 2020.
EP Extended European Search Report dated Nov. 4, 2022 pertaining to EP application No. 20745876.1 filed Jul. 19, 2021, pp. 1-7.
Weeber, F. et al. "Tumor Organoids as a Pre-clinical Cancer Model for Drug Discovery" Cell Chemical Biology, Sep. 21, 2017, pp. 1092-1100, vol. 24.
Yoo, J. et al. "315—Development Of T Cell-Pancreatic Cancer Organoid Co-Culture Model" Gastroenterology, Elsevier Inc, US, May 1, 2018, vol. 154(6).
Jayati Chakrabarti, et al., "Mouse-Derived Gastric Organoid and Immune Cell Co-culture for the Study of the Tumor Microenvironment" In: "Methods in Molecular Biology", Jun. 30, 2018 (Jun. 30, 2018), Humana Press, New York, NY, XP055727614.
Loryn Holokai Jayati Chakrabarti Julie Chang Mima Perusina Lanfranca Jiang Wang Timothy Frankel Syed Ahmad Yana Zavros: "Chemotherapy Induces Pancreatic Cancer Organoid Immune Evasion by Upregulating Programmed Death Ligand 1", FASEB Journal, vol. 32, No. S1, Apr. 1, 2018 (Apr. 1, 2018), pp. 607.01-607.01, XP009522711.

\* cited by examiner

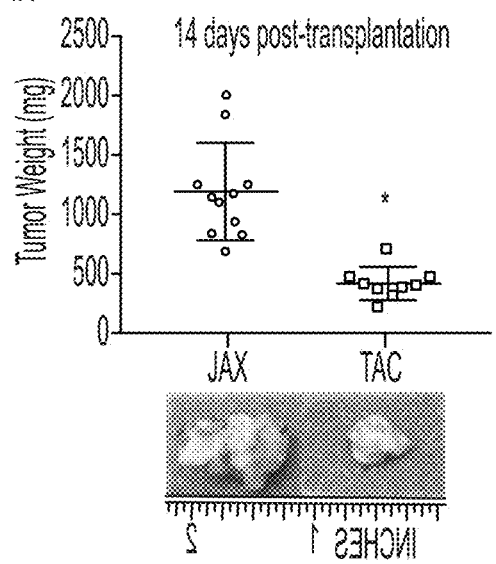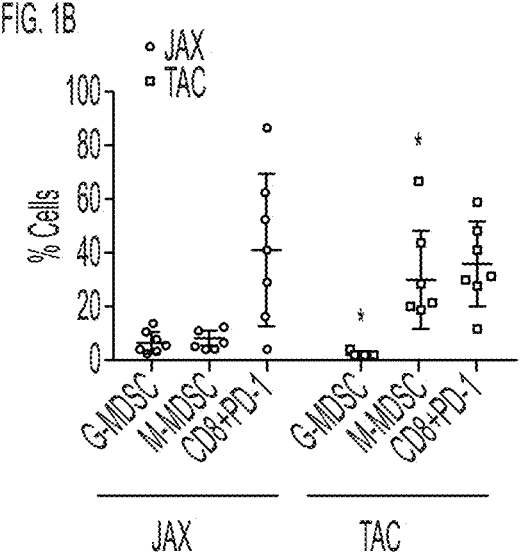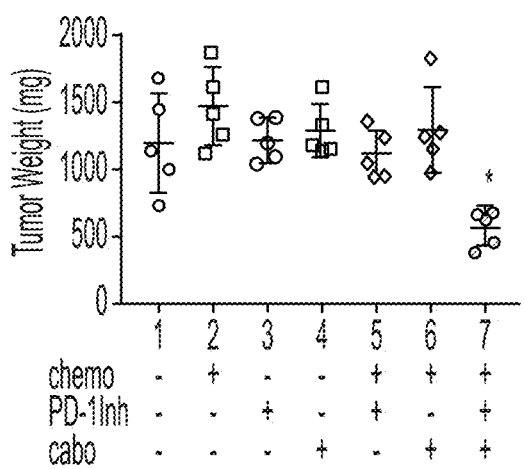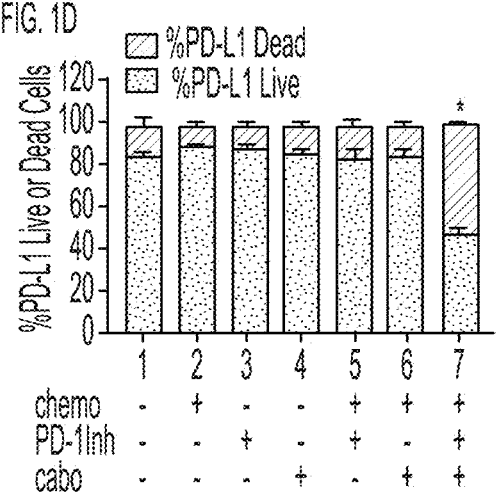

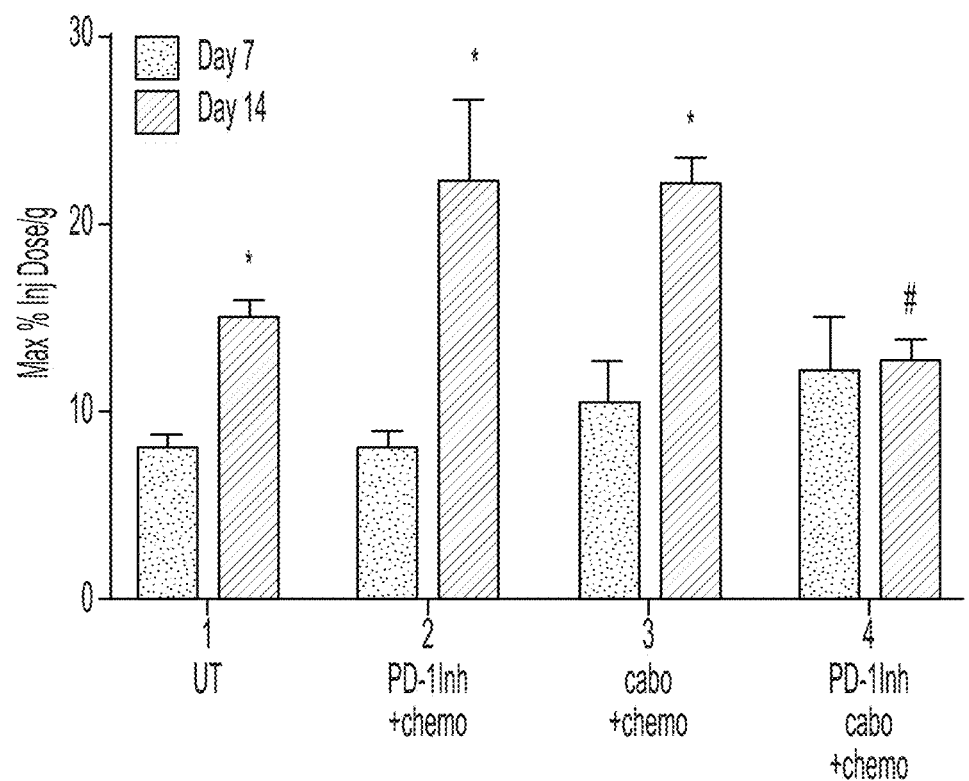

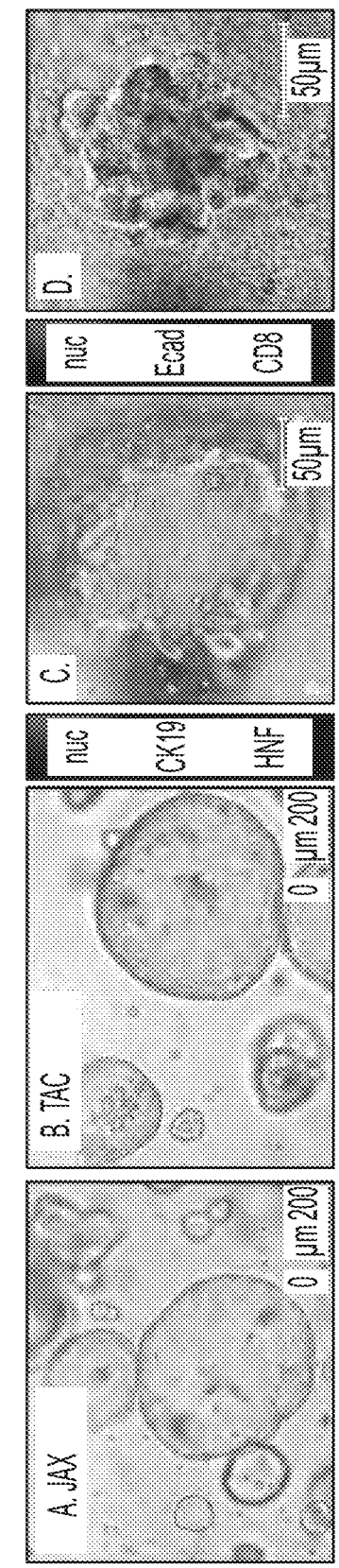

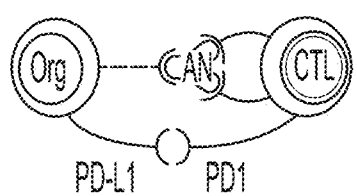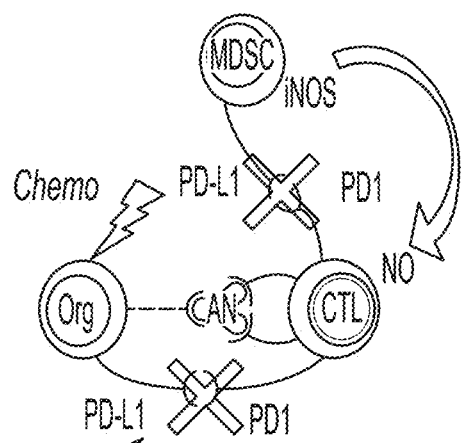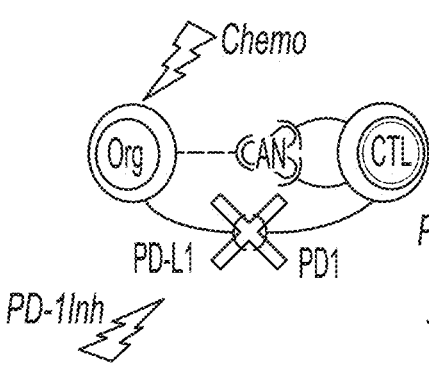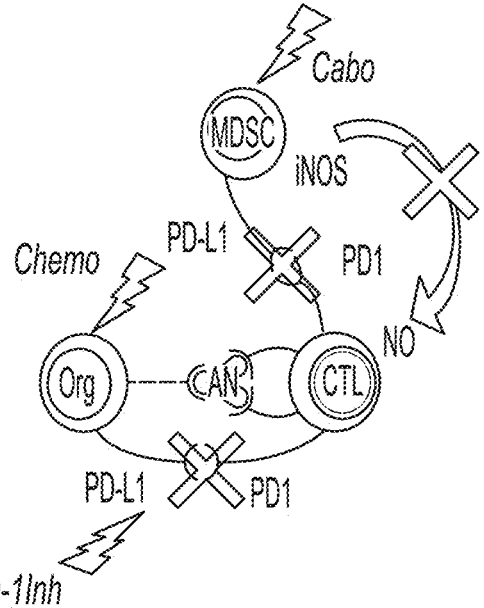
FIG. 3E

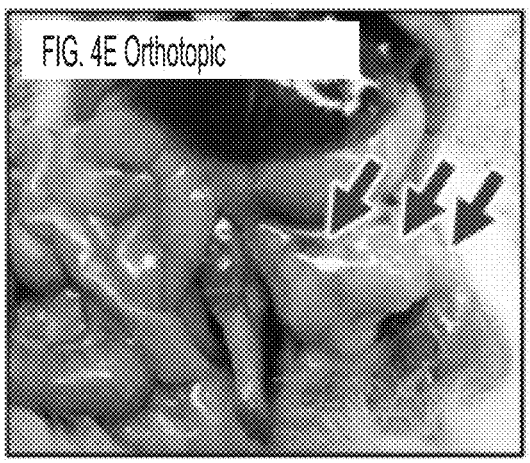
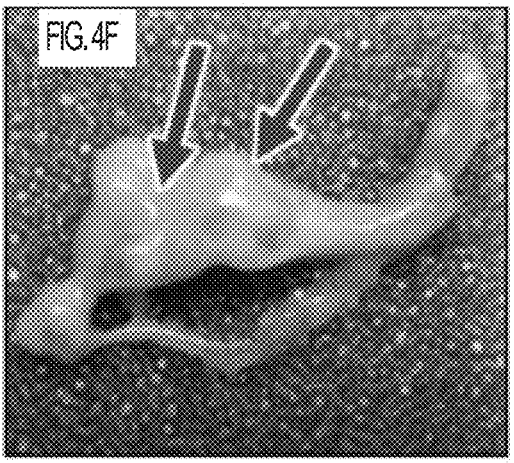
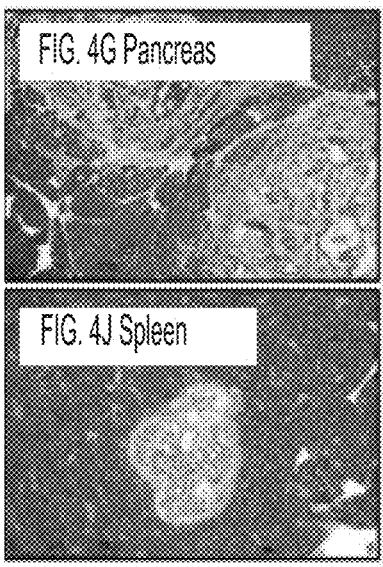
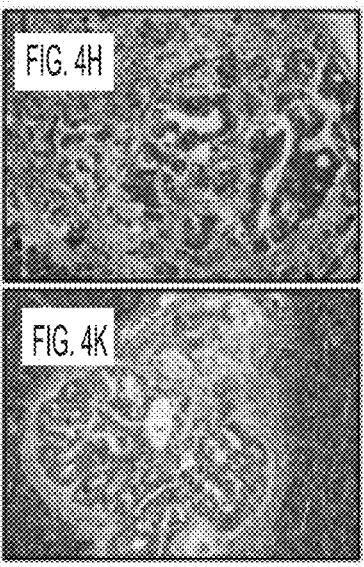
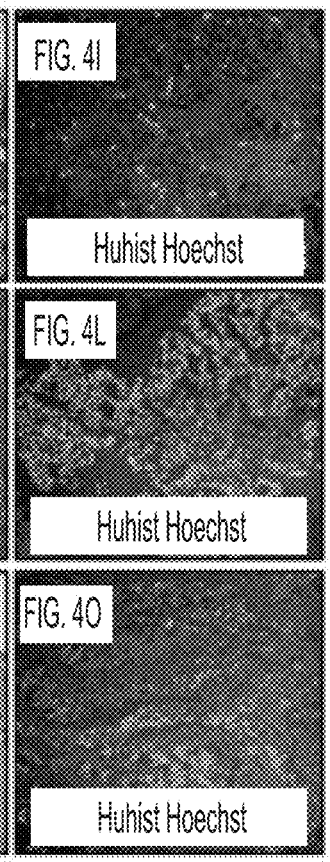
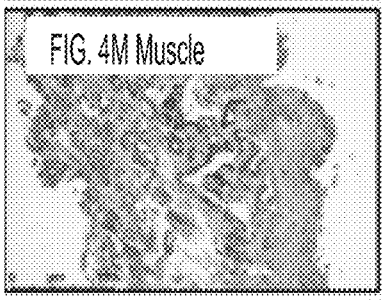

PDAC Patient Tumor and Organoid Response to Chemotherapy

| Patient | Patient Chemotherapy Treatment | Patient Response | Organoid Treatment | Organoid Response |
|---|---|---|---|---|
| P15T | Fulfirinox | Grade (1) almost complete response | Fulfirinox | Partial response |
| P10T | Gemcitabine Abraxane | Grade (2-3) no/poor response | Gemcitabine Abraxane | No response |
| P17T | Fulfirinox (adjuvant) | Pending | Fulfirinox | No response |
| P11T | Gemcitabine Abraxane | 0 | Gemcitabine Abraxane | Complete response |
| P24T | Fulfirinox | 2 | Fulfirinox | Partial response |
| P26T | Fulfirinox | 3 | Fulfirinox | Partial response |
| P28T | Gemcitabine Abraxane | 3 | Gemcitabine Abraxane | Partial response |
| P29T | Fulfirinox (adjuvant) | Pending | Fulfirinox | No response |
| P30T | Fulfirinox (adjuvant) | Pending | Fulfirinox | No response |

FIG. 5A

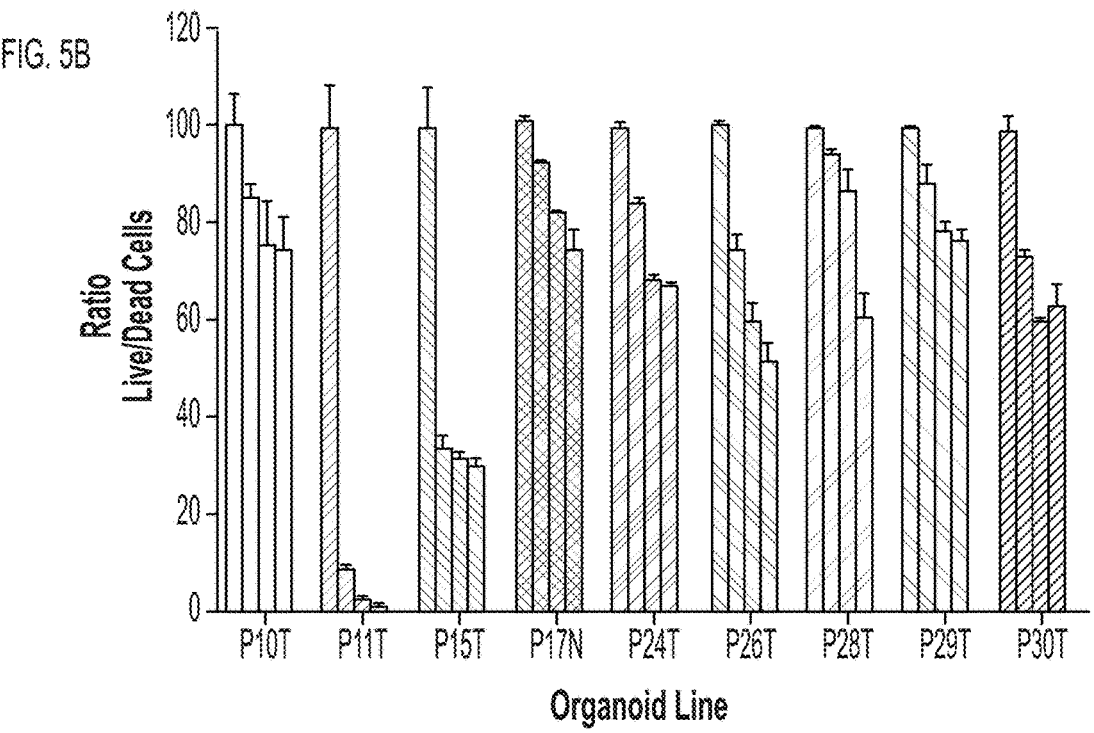

CD8     Ecad     Hoechst

CTLs

CD11b     Ecad     Hoechst

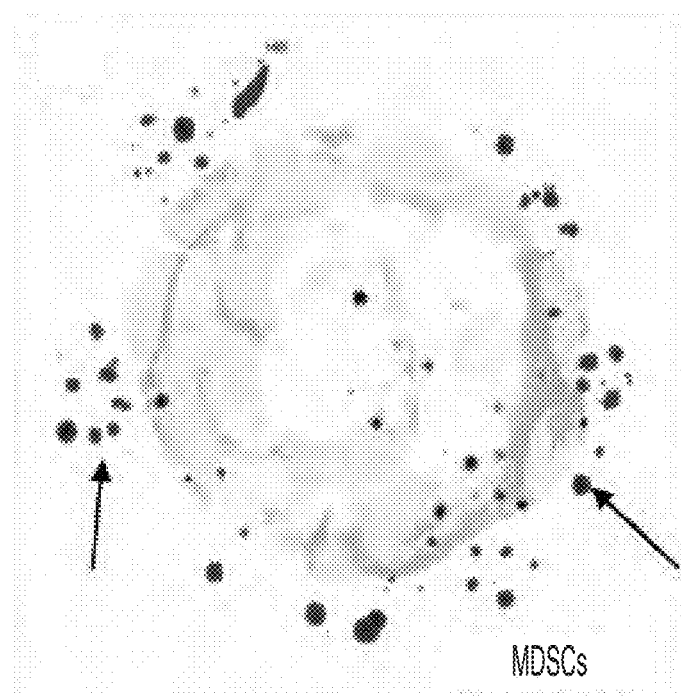
FIG. 6D
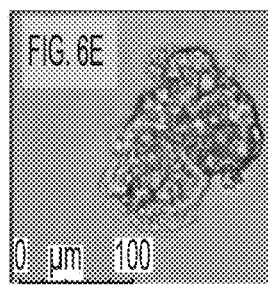
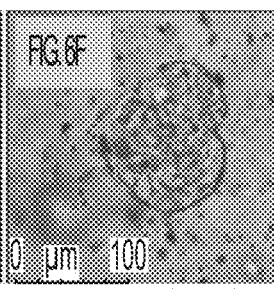
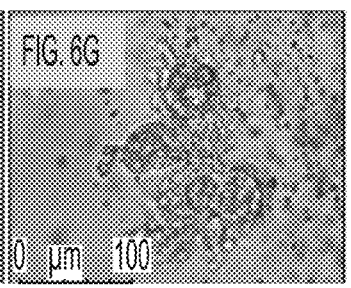
FIG. 6E  FIG. 6F  FIG. 6G

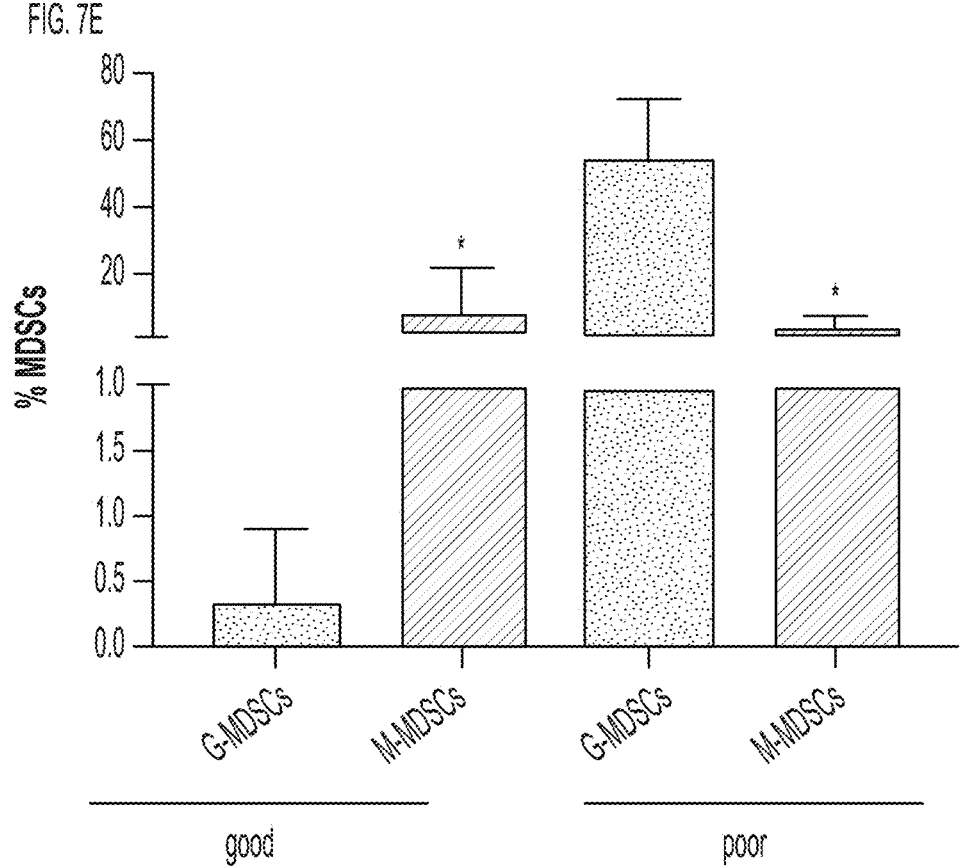

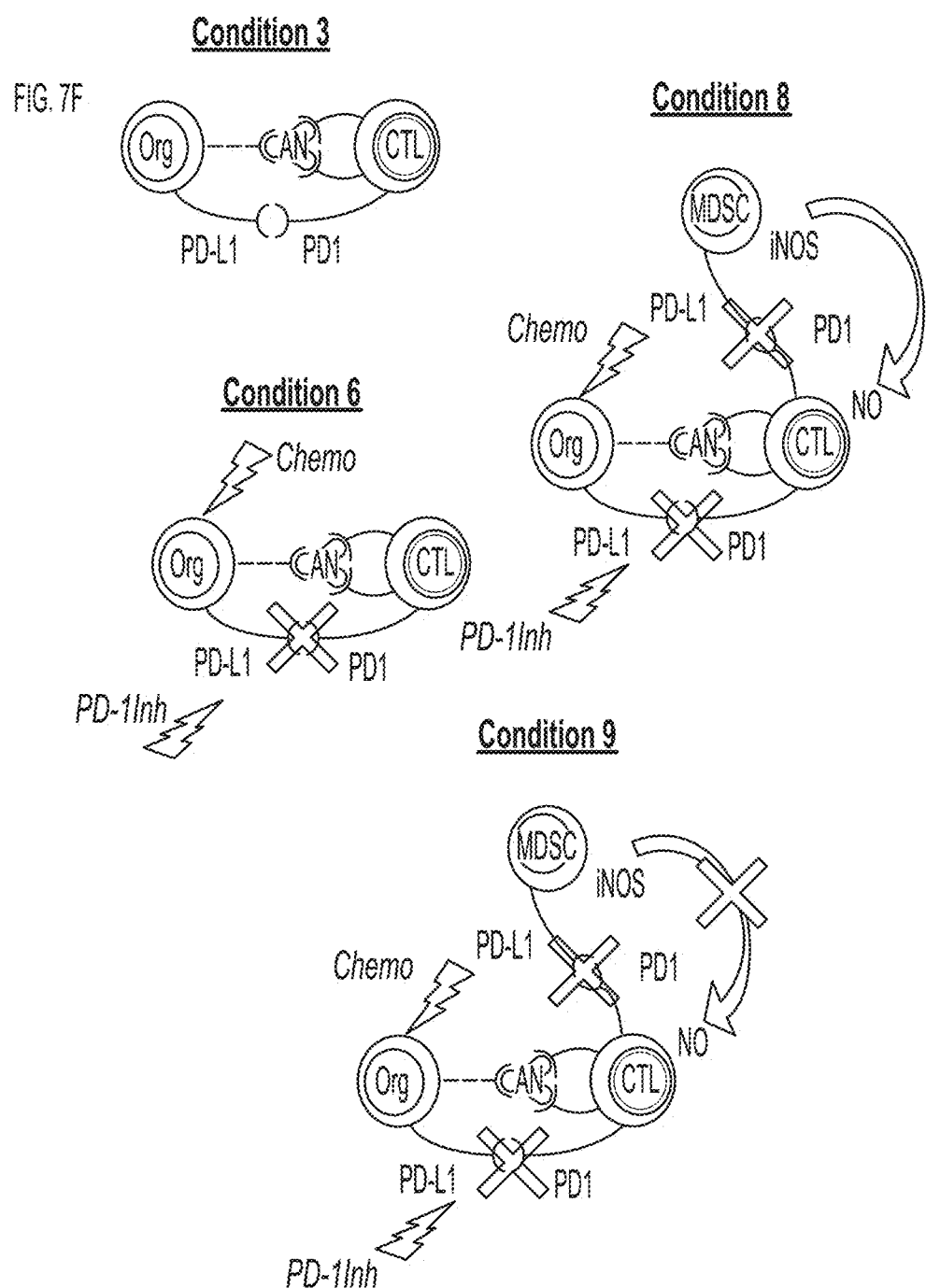

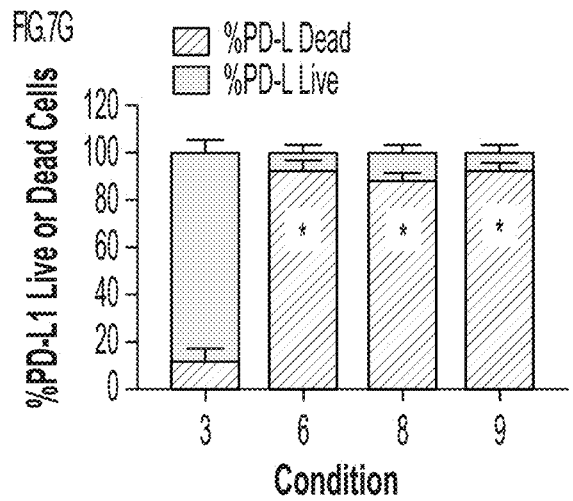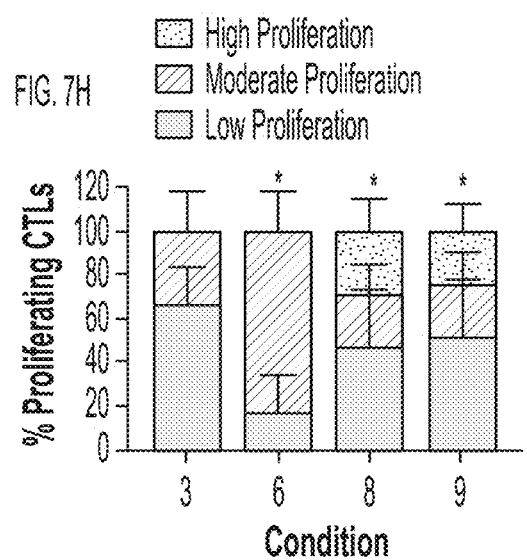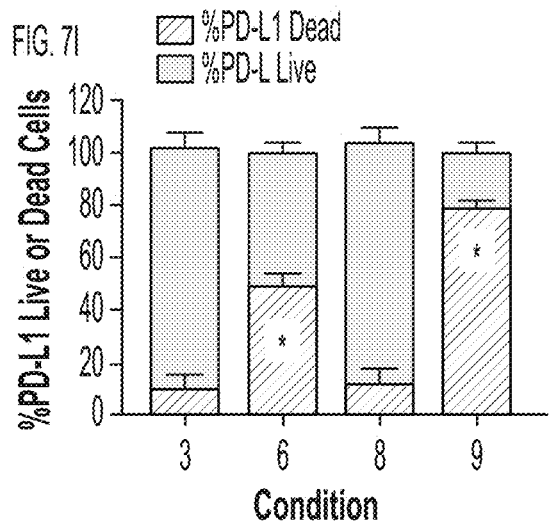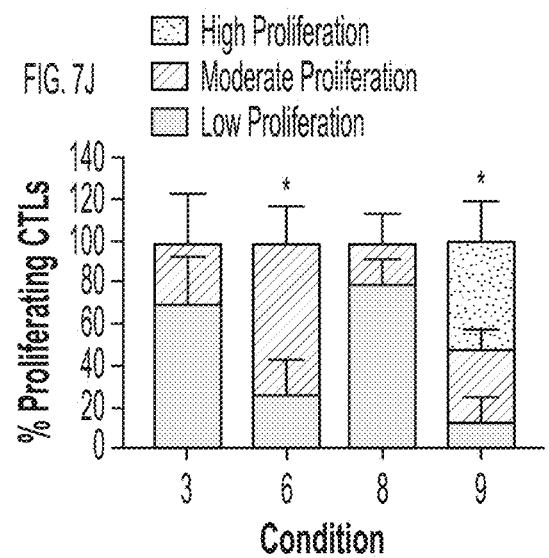

1. Org
2. Org + MDSC + MDSC
3. Org + MDSC + cabo
4. Org + MDSC + cabo + chemo

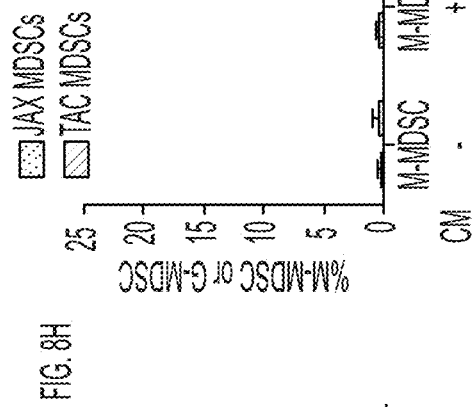
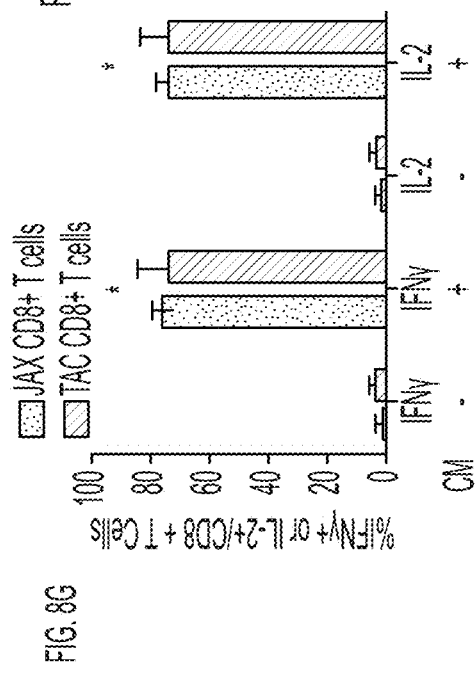
FIG. 8G
FIG. 8H
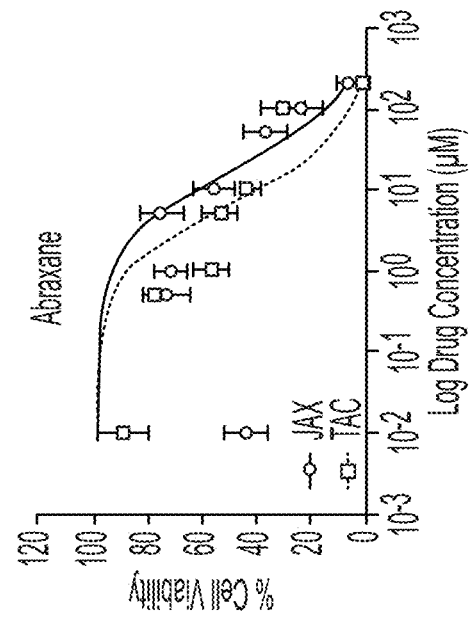
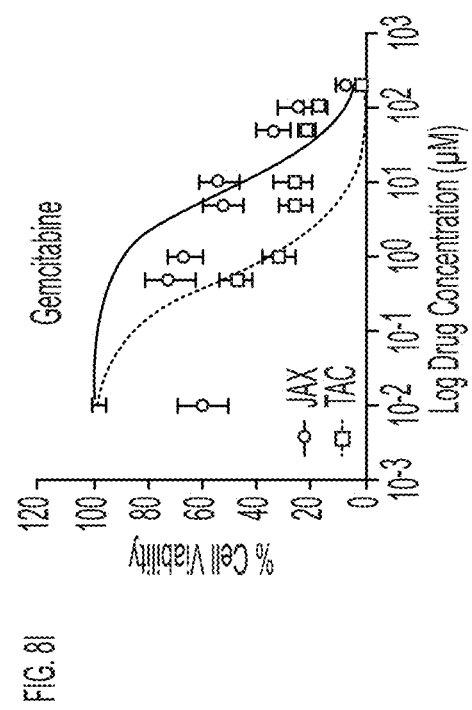
FIG. 8I

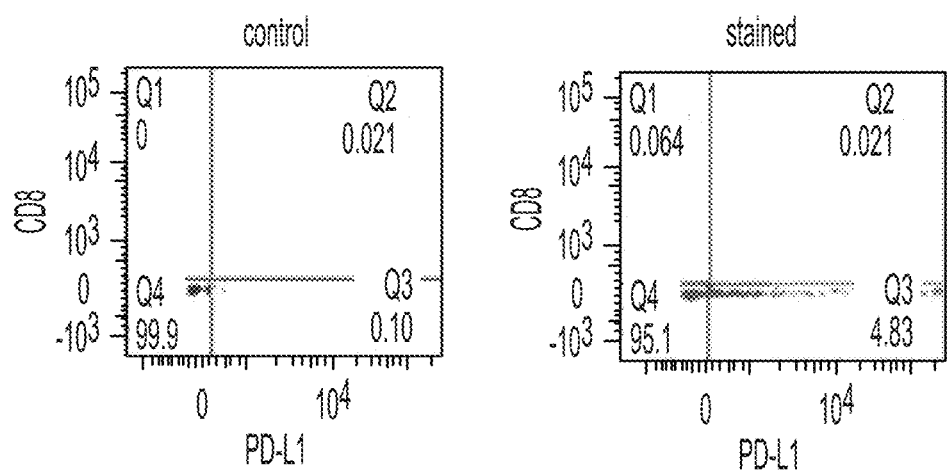
FIG. 9A. P10T
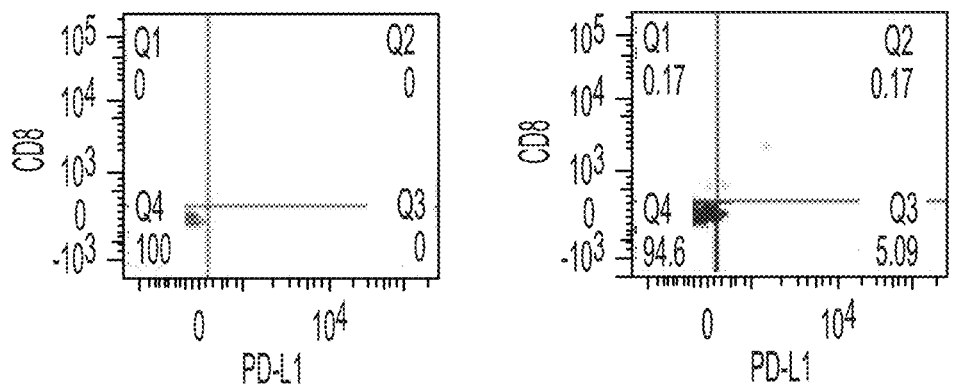
FIG. 9B. P17T
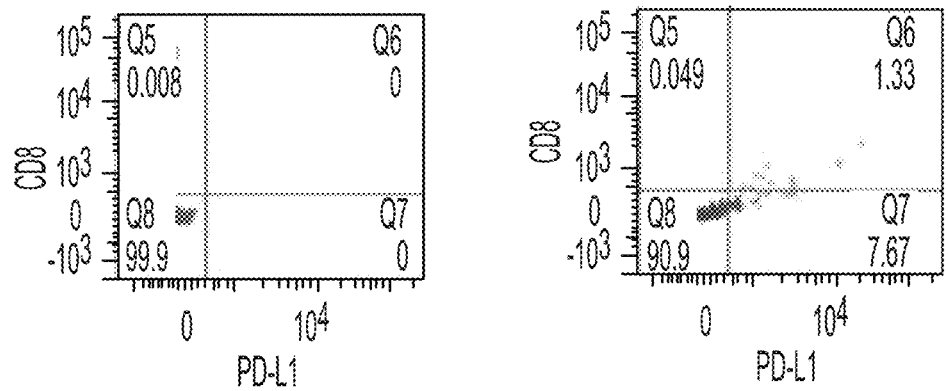
FIG. 9C. P26T
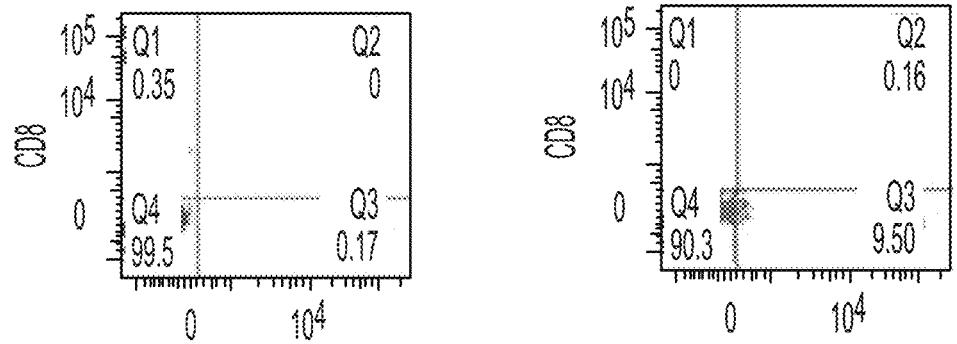
FIG. 9D. P24T

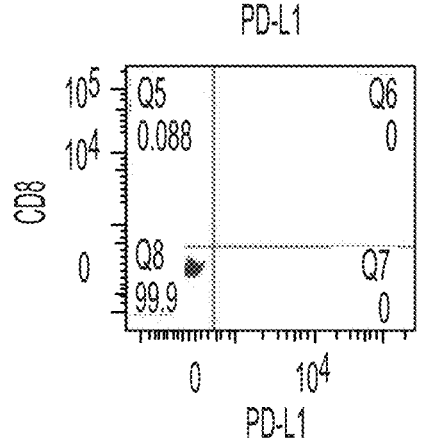
FIG. 9E. P28T
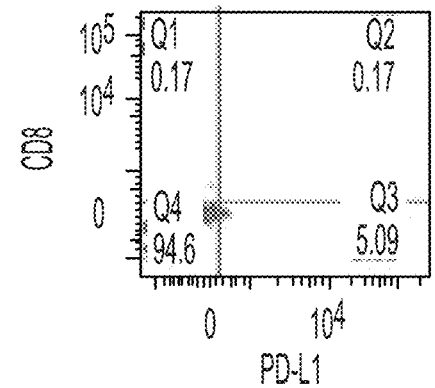
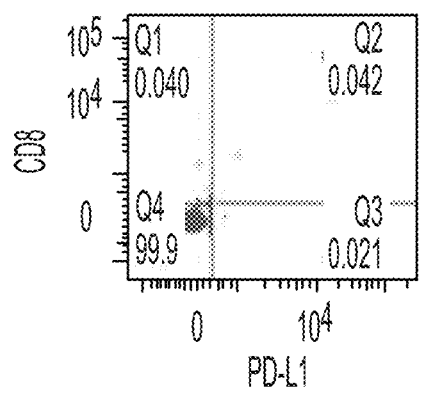
FIG. 9F. P29T
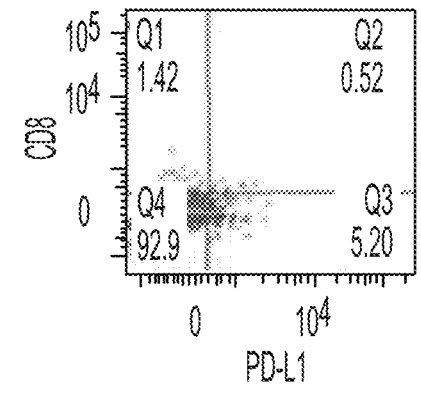
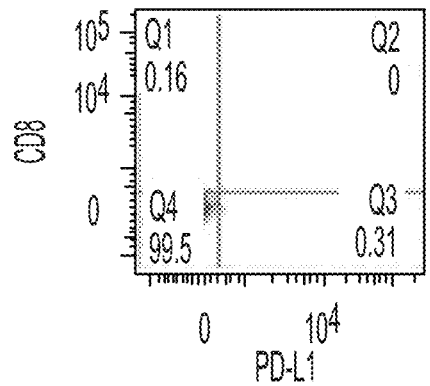
FIG. 9G. P30T
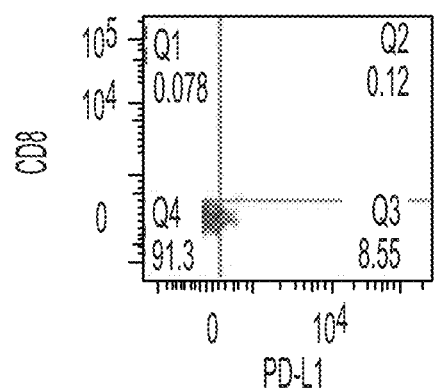

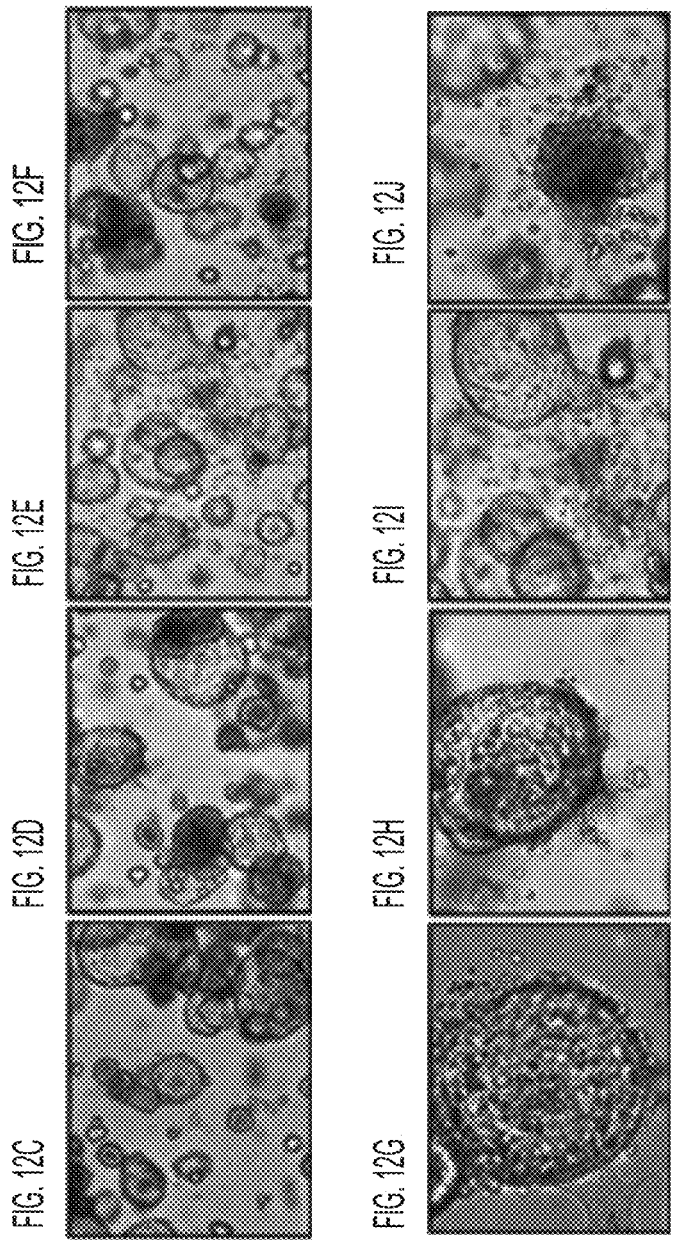

AUTOLOGOUS TUMOR ORGANOID AND IMMUNE CELL CO-CULTURES AND METHODS OF USE AS PREDICTIVE MODELS FOR PANCREATIC CANCER TREATMENT

CROSS-REFERENCE TO RELATED APPLICATIONS

This application is a § 371 National Stage Application of PCT/US2020/014925, filed Jan. 24, 2020, and claims priority to U.S. Provisional Application Ser. No. 62/796,307, filed Jan. 24, 2019, each of which is incorporated herein by reference in its entirety.

BACKGROUND

Pancreatic cancer is currently the third most common cause of cancer-related death in the United States. Pancreatic ductal adenocarcinoma (PDAC) is one of the most lethal malignancies, with an approximate 5-year survival rate of only 9%, despite therapeutic intervention. The dismal response of PDAC to existing treatments contributes to its poor prognosis and renders this disease an unmet medical challenge.

Tumors can evade immune surveillance by expressing immune checkpoint molecules, such as programmed cell death ligand 1 (PD-L1). PD-L1 interacts with the T cell protein programmed cell death 1 (PD-1), leading to inhibition of CD8+ cytotoxic T lymphocyte proliferation, survival, and effector function. Although anti-PD1 antibodies have been tested in clinical trials for pancreatic cancer treatment, patients have failed to respond. While not desiring to be bound by theory, it is believed that the lack of success observed with this therapeutic approach may be due to other redundant immune suppressive mechanisms at play.

Multiple suppressive immune cell types including macrophages, myeloid derived suppressor cells (MDSCs), and regulatory T cells (Tregs) accumulate in early pancreatic intraepithelial neoplasia (PanIN), the precursor lesion to pancreatic cancer, and persist through cancer progression. In humans and mice, two distinct subset of MDSCs exist: monocytic-MDSCs (M-MDSCs) and granulocytic-MDSCs (G-MDSCs). In particular, G-MDSCs are associated with a poor prognosis in pancreatic cancer.

Depletion of myeloid cells impairs tumor growth at different stages of pancreatic carcinogenesis. MDSCs are known to block CD8+ T cell anti-tumor activity through L-arginine and L-cysteine sequestration, as well as reactive oxygen species (ROS). Preclinical mouse models have similarly demonstrated that targeting the MDSC population enables an endogenous T cell response in PDAC. Further, PDAC patients who exhibit reduced levels of CD8+ T cells also exhibit elevated levels of MDSCs.

Particularly in view of the late state diagnosis and resistance to chemotherapy associated with pancreatic cancer, an urgent need exists for improved preclinical models for use in modeling the tumor microenvironment, predicting patient response to targeted cancer therapies, and identifying new therapies.

SUMMARY

Provided herein is a tumor organoid-immune cell co-culture that more accurately mimics the pancreatic tumor microenvironment, and methods for producing the same. The presently described co-cultures have application in predicting a patient's response to a candidate therapy, predicting a patient's cancer prognosis, and identifying new therapies effective for the treatment of pancreatic cancer.

In one embodiment, a method for preparing an autologous pancreatic tumor organoid and immune cell co-culture that mimics the pancreatic tumor microenvironment is provided, the method comprising: culturing pancreatic tumor cells obtained from a patient in culture media to provide a pancreatic tumor organoid and organoid-conditioned media; pulsing dendritic cells derived from the patient with a portion of the organoid-conditioned media; contacting the pulsed dendritic cells with cytotoxic T lymphocytes (CTLs) obtained from the patient in the organoid-conditioned media to activate the CTLs; isolating the activated CTLs; and co-culturing the pancreatic tumor organoid with (1) the activated CTLs, and (2) myeloid derived suppressor cells (MDSCs) derived from the patient, to obtain an autologous pancreatic tumor organoid and immune cell co-culture that mimics the pancreatic tumor microenvironment.

In another embodiment, a method of treating pancreatic cancer in a patient in need thereof, the method comprising administering to the patient a combination therapy comprising: an effective amount of an inhibitor of programmed cell death ligand 1 (PD-L1)/programmed cell death 1 (PD-1) interaction; and an effective amount of an inhibitor of granulocytic MDSCs (G-MDSCs).

In another embodiment, a method for determining whether a pancreatic cancer patient is likely to benefit from a candidate therapy is provided, comprising: providing an autologous pancreatic tumor organoid and immune cell co-culture comprising at least one pancreatic tumor organoid cultured from the patient's pancreatic tumor cells, autologous cytotoxic T lymphocytes (CTLs) activated by dendritic cells pulsed in tumor organoid-conditioned media, and myeloid derived suppressor cells (MDSCs) differentiated from autologous peripheral blood mononuclear cells (PBMCs) cultured in tumor organoid-conditioned media; contacting the autologous pancreatic tumor organoid and immune cell co-culture with the candidate therapy; detecting one or more changes in the autologous pancreatic tumor organoid and immune cell co-culture indicative of therapeutic efficacy of the candidate therapy against the autologous pancreatic tumor organoid and immune cell co-culture; and determining that the patient is likely to benefit from the candidate therapy when the one or more changes indicative of therapeutic efficacy are detected.

In another embodiment, an autologous pancreatic tumor organoid and immune cell co-culture that mimics a patient's pancreatic tumor microenvironment is provided, comprising: at least one pancreatic tumor organoid cultured from the patient's pancreatic tumor cells; autologous cytotoxic T lymphocytes (CTLs) activated by dendritic cells pulsed in tumor organoid-conditioned media; and myeloid derived suppressor cells (MDSCs) differentiated from autologous peripheral blood mononuclear cells (PBMCs) cultured in tumor organoid-conditioned media.

In another embodiment, a method of screening for effective pancreatic cancer therapies is provided, comprising: providing an autologous pancreatic tumor organoid and immune cell co-culture, comprising at least one pancreatic tumor organoid cultured from the patient's pancreatic tumor cells, autologous cytotoxic T lymphocytes (CTLs) activated by dendritic cells pulsed in tumor organoid-conditioned media, and myeloid derived suppressor cells (MDSCs) differentiated from autologous peripheral blood mononuclear cells (PBMCs) cultured in tumor organoid-conditioned media; contacting the autologous pancreatic tumor organoid and immune cell co-culture with the candidate therapy; detecting one or more changes in the autologous pancreatic tumor organoid and immune cell co-culture indicative of therapeutic efficacy of the candidate therapy against the autologous pancreatic tumor organoid and immune cell co-culture; and identifying the candidate therapy as an effective pancreatic cancer therapy when the one or more changes indicative of therapeutic efficacy are detected.

These and other embodiments and aspects will be clarified and better understood by reference to the figures and detail description set forth below. Figures are provided to illustrate technical problems in the art as well as specific embodiments and aspects of the invention and should not be construed as limiting the full scope of the claims appended hereto.

BRIEF DESCRIPTION OF THE DRAWINGS

FIGS. 1A-1H. PDAC tumor growth and therapy responses in JAX and TAC mice. (FIG. 1A) Tumor weights 14 days post-orthotopic transplantation in JAX and TAC mice. (FIG. 1B) Flow cytometric analysis of G-MDSC, M-MDSCs, CD8+PD-1-expressing immune cells isolated from JAX and TAC mouse tumors. *P<0.05 compared to JAX mice, n=5 mice per group. (FIG. 1C) Tumor weights in mice treated with combinations of chemotherapy (gemcitabine/epothilone A), PD-1Ihn and cabozantanib (cabo). *P<0.05 compared to untreated mice (group 1), n=5 mice per group. (FIG. 1D) Flow cytometric analysis of the percentage of live and dead PD-L1 expressing cells within mouse tumors. *P<0.05 compared to untreated mice (group 1), n=5 mice per group. (FIG. 1E) Flow cytometric histograms demonstrating the distribution of G-MDSCs in tumors collected from untreated and combination (chemo, PD-1Inh, cabo) treated mice. (FIG. 1F) Quantification of the percent of G-MDSCs in treated mice. *P<0.05 compared to untreated mice (group 1), n=5 mice per group. (FIG. 1G) Immunohistochemical stain of CD8+/PCNA+ cells within tumor tissue collected from untreated and combination treated mice. (FIG. 1H) Quantification of CD8+/PCNA+ cells within tumor tissue collected from treated mice. *P<0.05 compared to untreated mice (group 1), n=5 mice per group.

FIGS. 2A-2E. PET-FDG imaging of PDAC tumor growth in JAX mice at 7 and 14 days. (FIG. 2A) PET-FDG image of an untreated JAX mouse on day 7 that was orthotopically transplanted with 7940b murine PDAC cells. (FIG. 2B) PET-FDG image of the same untreated JAX mouse on day 14. (FIG. 2C) PET-FDG image of a JAX mouse treated with gemcitabine, epothilone A, nivolumab and cabozantinib on day 7 that was orthotopically transplanted with 7940b murine PDAC cells. (FIG. 2D) PET-FDG image of the same JAX mouse treated with gemcitabine, epothilone A, nivolumab and cabozantinib on day 14. (FIG. 2E) Maximum % injected dose/g. *P<0.05 compared to day 7 group, #P<0.05 compared to day 14 group, n=4 mice per group.

FIGS. 3A-3M. Murine-derived autologous pancreatic cancer organoid/immune cell co-cultures. Light micrographs of organoids derived from (FIG. 3A) JAX and (FIG. 3B) TAC pancreatic cancer tumors. Immunofluorescence staining of pancreatic organoids for expression of (FIG. 3C) HNF1β and cytokeratin 19 (CK19) or (FIG. 3D) CD8 and E-cadherin (Ecad). Nuclei stain shown by Hoechst. (FIG. 3E) Schematic representation of experimental conditions 3, 6, 10 and 11 used in organoid/immune cell co-cultures. Percent of live/dead PD-L1-expressing organoids in co-cultures derived from (FIG. 3F, FIG. 3G) JAX and (FIG. 3H, FIG. 3I) TAC mice. Percent of CD8+ T cell proliferation in co-cultures derived from (FIG. 3J, FIG. 3K) JAX and (FIG. 3L, FIG. 3M) TAC mice. *P<0.05 compared to condition 3, n=5 individual co-cultures per group.

FIGS. 5A-5C. Characterization of PDAC patient tumor and organoid response to chemotherapeutics. (FIG. 5A) Patient and matching organoid treatments and responses. (FIG. 5B) Ratio of live/dead human-derived PDAC organoids after patient-matched chemotherapy. (FIG. 5C) Table of patient tumor staging, tumor cell differentiation, and invasion of adjacent tissue and lymph nodes.

FIGS. 6A-6G. Representative image of human-derived autologous pancreatic cancer organoid/immune cell co-cultures. (FIG. 6A) Immunofluorescence stain of human-derived autologous pancreatic cancer organoid/immune cell co-cultures with antibodies specific for CD8, E cadherin (Ecad), and Hoechst. (FIG. 6B) 3 dimensional image of a PDAC organoid with autologous CTLs. (FIG. 6C) Immunofluorescence stain of human-derived autologous pancreatic cancer organoid/immune cell co-cultures with antibodies specific for CD11b, Ecad, and Hoechst. (FIG. 6D) 3 dimensional image of a PDAC organoid with autologous MDSCs. Light micrographs of (FIG. 6E) human-derived PDAC organoids alone, (FIG. 6F) co-cultured with autologous CTLs, and (FIG. 6G) or co-cultured with autologous CTLs, nivolumab, cabozantinib, and chemotherapy.

FIGS. 7A-7J. Human-derived autologous pancreatic cancer organoid/immune cell co-cultures. CyTOF dot plot analysis of the G-MDSCs present in the immune microenvironment from patients with (FIG. 7A) good or (FIG. 7B) poor prognosis. (FIG. 7C) CyTOF analysis of M-MDSCs and G-MDSCs using cell isolated from patient tumor tissue. (FIG. 7E) Flow cytometric analysis of G-MDSCs and M-MDSCs in a co-culture of autologous PDAC organoids and immune cells derived from patients with good or poor prognosis. (FIG. 7F) Schematic representation of experimental conditions 3, 6, 8 and 9 used in organoid/immune cell co-cultures. Organoid/immune cell co-cultures derived from patients with a good prognosis were analyzed for (FIG. 7G) percent of live/dead PD-L1-expressing human-derived PDAC organoids in co-culture with autologous immune cells. (FIG. 7H) Percent of proliferating CTLs in co-culture with autologous MDSCs and human-derived PDAC organoids. Organoid/immune cell co-cultures derived from patients with a poor prognosis were analyzed for (FIG. 7I) percent of live/dead PD-L1-expressing human-derived PDAC organoids in co-culture with autologous immune cells. (FIG. 7J) Percent of proliferating CTLs in co-culture with autologous MDSCs and human-derived PDAC organoids. *P<0.05 compared to condition 3.

FIGS. 8A-8I. Murine-derived autologous pancreatic cancer organoid/immune cell co-cultures. Percent of live/dead PD-L1-expressing organoids in co-cultures derived from (FIG. 8A) JAX and (FIG. 8B) TAC mice. (FIG. 8C) Autologous organoid/MDSCs co-cultures derived from JAX and TAC mice were treated with either chemotherapy, cabo, or a combination thereof (conditions 1-4). Percent of live/dead PD-L1-expressing organoids in co-cultures derived from (FIG. 8D) JAX and (FIG. 8E) TAC mice in response to conditions 1-4. (FIG. 8F) Percent of zombie positive (dead) MDSCs in co-cultures derived from JAX and TAC mice in response to conditions 1-4. *P<0.05 compared to condition 1, n=3 individual co-cultures per group. Flow cytometric analysis of (FIG. 8G) IFNγ and IL-2 expressing CD8+ T cells and (FIG. 8H) M-MDSCs and G-MDSCs and in response to conditioned and unconditioned media. *P<0.05 compared to without conditioned media, n=3 individual co-cultures per group. (FIG. 8I) Dose response curves of PDAC organoids derived from JAX and TAC mouse tumors in response to gemcitabine (left panel) and abraxane (right panel).

FIGS. 9A-9G. Expression of PD-L1 in organoids from human-derived PDAC co-cultures. Flow cytometric dot plots generated from cells collected from organoid/immune cell co-cultures from (FIG. 9A) P10T, (FIG. 9B) P17T, (FIG. 9C) P26T, (FIG. 9D) P24T, (FIG. 9E) P28T, (FIG. 9F) P29T, and (FIG. 9G) P30T lines. Shown are the unstained controls (left panels) and stained samples (right panels).

(FIG. 11A) Percent of zombie positive (dead) MDSCs in co-cultures derived from patients with either a low or high stage tumor grade. *P<0.05 compared to condition 1, n=3 individual co-cultures per group. (FIG. 11B) Flow cytometric analysis of IFNγ and IL-2 expressing CD8+ T cells in response to conditioned and unconditioned media. *P<0.05 compared to without conditioned media.

FIGS. 12A-12L. Mouse-derived pancreatic cancer organoid/immune cell co-cultures. (FIG. 12A) Experimental design and timing of the culture of DCs, CTLs, and MDSCs over 7 days with co-culture of cancer organoids. (FIG. 12B) Experimental conditions 1-4 for co-cultures. Representative images of organoid/immune cell co-cultures in response to (FIG. 12C, FIG. 12G) organoid+CTLs untreated, (FIG. 12D, FIG. 12H) organoids+CTLs treated with PD-1 inhibitor, (FIG. 12E, FIG. 12I) organoids+CTLs+MDSCs treated with PD-1 inhibitor, and (FIG. 12F, FIG. 12J) organoids+CTLs+MDSCs treated with PD-1 inhibitor plus cabozantinib showing organoid death. (FIG. 12K, FIG. 12L) Increased CTL proliferation as measured by CFSE in experimental condition 4.

DETAILED DESCRIPTION

Figure 1E:
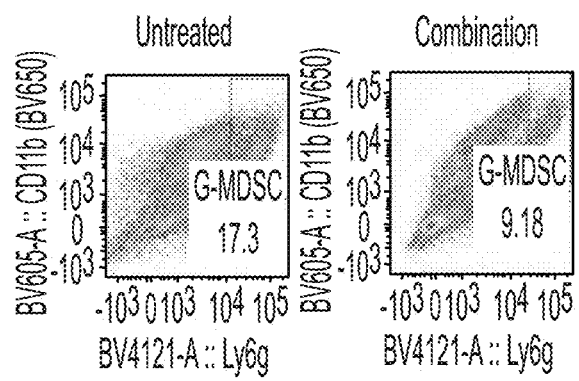

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

"Pancreatic cancer," as used herein, includes both exocrine and endocrine tumors. Exocrine tumors include pancreatic ductal adenocarcinoma (PDAC), acinar cell carcinoma, intraductal papillary-mucinous neoplasm (IPMN), cystic tumors, and mucinous cystic neoplasm with an invasive adenocarcinoma. Other types of pancreatic cancer include pancreatoblastoma, sarcomas of the pancreas, and lymphoma. In a specific embodiment, the pancreatic cancer is PDAC.

"Organoids" are three-dimensional tissue-resembling cellular clusters derived from tissue or tumor specific stem cells that mimic the in vivo tumor characteristics, as well as tumor cell heterogeneity.

"Co-culture" refers to two or more cell types maintained in conditions suitable for their mutual growth.

"Subject" and "patient" are used interchangeably to refer to a human or any non-human animal (such as any mouse, rat, rabbit, dog, cat, cattle, swine, sheep, horse, or primate). In certain embodiments, the patient is a mammal, and more specifically a human. A subject can be a patient, which refers to a human presenting to a medical provider for diagnosis or treatment of a disease. A patient can be afflicted with or is susceptible to a disease or disorder but may or may not display symptoms of the disease or disorder.

An "effective amount" refers to an amount of a therapeutic agent that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by the skilled person that a therapeutically effective amount is typically administered via a dosing regimen comprising at least one unit dose.

"Treating," "treat," and "treatment" refer to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

"Autologous" refers to cells derived from the same subject or patient. For example, the tumor organoid and immune cell co-cultures described herein are developed using tumor cells obtained from a patient and cultured to obtain an organoid, together with immune cells obtained from or differentiated from cells obtained from the same patient.

When considering a cancer patient's prognosis, a "good prognosis" typically refers to a prognosis of no recurrence of disease and/or survival of the patient beyond a period of 5 years after therapeutic treatment. A "poor prognosis" typically refers to a prognosis of recurrence of disease before or after a period of 5 years after therapeutic treatment.

Pancreatic cancer staging is assessed based on location, size, and extent of primary tumor (T), presence or absence of regional lymph node metastasis (N), and presence or absence of distant metastasis (M). Stage 0 includes pancreatic cancers wherein a carcinoma is detected in situ, or the tumor is classified as PanINIII, without lymph node or distant metastasis (TisN0M0). Stage IA includes cancers wherein the primary tumor is limited to the pancreas and 2 cm or less in greatest dimension, without lymph node or distant metastasis (T1N0M0). Stage D3 includes cancers wherein the primary tumor is limited to the pancreas and more than 2 cm in greatest dimension, without lymph node or distant metastasis (T2N0M0). Stage IIA includes cancers wherein the tumor extends beyond the pancreas, but without involvement of the celiac axis or the superior mesenteric artery, without lymph node or distant metastasis (T3N0M0). Stage IIB includes any primary tumor, including wherein the tumor extends beyond the pancreas but without involvement of the celiac axis or the superior mesenteric artery, wherein regional lymph nodes are involved, but no other distant metastasis is present (T1N1M0; T2N1M0; T3N1M0). Stage III includes cancers wherein the tumor involves the celiac axis or the superior mesenteric artery and is an unresectable primary tumor, with or without regional lymph node involvement, but without distant metastasis (T4N0M0 or T4N1M0). Stage IV pancreatic cancer includes cancers of any type, with or without regional lymph node involvement, wherein distant metastasis is present (Any T, Any N, M1). See *Pancreatic Cancer Staging*, American Joint Committee on Cancer, available at cancerstaging.org. Generally, "low stage" pancreatic cancer refers to cancers wherein the primary tumor has not invaded the lymph nodes or metastasized to distant organs. "High stage" pancreatic cancer generally refers to cancers wherein lymph node and/or distant metastasis is indicated.

The presently disclosed studies use an autologous organoid/immune cell co-culture to investigate the pancreatic cancer immune microenvironment and its effect on anti-PD1 therapeutics.

Murine- and human-derived pancreatic cancer organoids and autologous immune cells were used to study the effect of G-MDSCs on the therapeutic efficacy of the immune checkpoint inhibitor nivolumab on PD-L1 expressing PDAC cells. JAX mice and patients with advanced stage tumors exhibited increased infiltration of G-MDSCs. In addition, PD-L1 expressing organoids derived from these JAX mice and patients with advanced stage tumors exhibited resistance to chemotherapy and/or nivolumab alone in immune co-cultures.

MDSCs have a remarkable ability to suppress T-cell response. A number of studies have reported that MDSCs block anti-cancer activity by expressing PD-L. In support of this evidence, JAX mice and patients with advanced stage tumors exhibited elevated infiltration of G-MDSCs. Additionally, treatment with chemotherapy, nivolumab, and cabozantinib exhibited: 1) significantly increased PD-L1- and G-MDSC-expressing cell death, 2) increased CTL proliferation, and 3) overall tumor regression or PD-L1 expressing cancer organoid death. Collectively, these studies suggest that a combinatorial treatment that both inhibits or depletes G-MDSCs and inhibits the PD-1/PD-L1 interaction is beneficial to boost T cell effector function and proliferation to target and kill PD-L1-expressing pancreatic cancer cells.

The presently disclosed protocol provides pancreatic cancer tumor organoid/immune cell co-cultures that may be: 1) rapidly grown and tested to inform clinicians of patient treatment within about 6 days of surgery, and 2) co-cultured with the patient's own immune cells. The latter is advantageous because it allows study of the interaction between the cancer cells and the immune cell compartment within the patient's own tumor microenvironment, providing a model for personalized medicine.

Autologous Tumor Organoid and Immune Cell Co-Cultures

In one embodiment, a method for preparing an autologous pancreatic tumor organoid and immune cell co-culture that mimics the pancreatic tumor microenvironment is provided, the method comprising: culturing pancreatic tumor cells obtained from a patient in culture media to provide a pancreatic tumor organoid and organoid-conditioned media; pulsing dendritic cells derived from the patient with a portion of the organoid-conditioned media; contacting the pulsed dendritic cells with cytotoxic T lymphocytes (CTLs) obtained from the patient in the organoid-conditioned media to activate the CTLs; isolating the activated CTLs; and co-culturing the pancreatic tumor organoid with (1) the activated CTLs, and (2) myeloid derived suppressor cells (MDSCs) derived from the patient, to obtain an autologous pancreatic tumor organoid and immune cell co-culture that mimics the pancreatic tumor microenvironment.

The presently disclosed co-cultures employ dendritic cells pulsed with organoid-conditioned media as the antigen-presenting cells for expanding autologous CTLs.

In embodiments, pancreatic tumor cells are obtained from a patient via biopsy. The biopsy tissue is processed according standard protocols to provide tumor cells. Tumor cells are cultured in media selected for organoid growth. In embodiments, human pancreatic culture media suitable for use comprises DMEM/F12 media supplemented with one or more of ascorbic acid, insulin, hydrocortisone, FGF2, ATRA, Y27632, FGF10, penicillin/streptomycin, gentamicin/amphotericin B, glutamax, BPE, R-Spondin, and Wnt conditioned media. In embodiments, mouse pancreatic culture media suitable for use comprises DMEM/F12 media supplemented with one or more of penicillin/streptomycin, B27, N-acetyl cysteine, gastrin 50, EGF, R-Spondin, Noggin, FGF10, and nicotinamide.

As tumor organoids are cultured, organoid-conditioned media can be removed from the culture for use in the methods described herein. Organoid-conditioned media advantageously comprises secreted cytokines and tumor antigens that mimic the tumor microenvironment of the patient from whom the tumor cells were obtained.

In embodiments, culturing pancreatic tumor cells in the culture media comprises suspending pancreatic tumor cells in a basement membrane matrix, over which culture media is layered. In embodiments, co-culturing the pancreatic tumor organoid with the activated CTLs and the MDSCs comprises suspending the pancreatic tumor organoid, activated CTLs, and MDSCs in a basement membrane matrix and overlaying pancreatic culture media. Suitable basement membrane matrices include, but are not limited to, Matrigel® (Corning Life Sciences) and Cultrex® (Trevigen).

Autologous immune cells are obtained from biological samples obtained from the patient. In embodiments, the biological sample is selected from the group consisting of bone marrow, whole blood, spleen, and tumor tissue. In a specific embodiment, the patient or subject is a mouse and the immune cells are obtained from bone marrow and/or spleen. In another specific embodiment, the patient or subject is a human and the immune cells are obtained from whole blood and/or tumor tissue. In a more specific embodiment, the immune cells are obtained from a whole blood sample.

In embodiments, a patient's peripheral blood mononuclear cells (PBMCs) are isolated from the whole blood sample and further processed to provide autologous CTLs, monocytes, MDSCs, and dendritic cells.

In embodiments, patient PBMCs are cultured in monocyte media to derive monocytes, which serve as progenitors for differentiation into MDSCs. In embodiments, MDSCs are differentiated from monocytes by culturing in a portion of organoid-conditioned media retained from the production of the tumor organoid from the patient's cancer cells. In embodiments, the culture medium may comprise about 50%, 60%, 70%, 80%, 90%, 95%, 96%, 97%, 98%, or 99% organoid-conditioned media, the balance of the composition corresponding to unconditioned culture media. Suitable monocyte specific media are known in the art. See, for example, In embodiments, the differentiated MDSCs comprise granulocytic MDSCs (G-MDSCs) and/or monocytic MDSCs (M-MDSCs). In a specific embodiment, the MDSCs are G-MDSCs.

In embodiments, patient PBMCs are cultured in dendritic cell media to derive dendritic cells. The dendritic cells are then pulsed with tumor-organoid conditioned media to allow for tumor antigen uptake by the dendritic cells. In embodiments, the culture medium may comprise about 50%, 60%, 70%, 80%, 90%, 95%, 96%, 97%, 98%, or 99% organoid-conditioned media, the balance of the composition corresponding to unconditioned dendritic cell media.

Patient PBMCs may be further processed via CD8+ T cell selection protocols known in the art to extract isolated autologous CTLs.

In embodiments, an autologous pancreatic tumor organoid and immune cell co-culture that mimics a patient's pancreatic tumor microenvironment is provided, comprising: at least one pancreatic tumor organoid cultured from the patient's pancreatic tumor cells; autologous cytotoxic T lymphocytes (CTLs) activated by dendritic cells pulsed in tumor organoid-conditioned media; and myeloid derived suppressor cells (MDSCs) differentiated from autologous peripheral blood mononuclear cells (PBMCs) cultured in tumor organoid-conditioned media. In embodiments, the MDSCs are G-MDSCs.

Methods of Treating Pancreatic Cancer

In embodiments, a method of treating pancreatic cancer in a patient in need thereof is provided, the method comprising administering to the patient a combination therapy comprising: an effective amount of an inhibitor of programmed cell death ligand 1 (PD-L1)/programmed cell death 1 (PD-1) interaction; and an effective amount of an inhibitor of MDSCs. In a specific embodiment, the MDSCs are granulocytic MDSCs (G-MDSCs).

Various inhibitors of PD-L1/PD-1 interaction are known in the art. In embodiments, the inhibitor of PD-L1/PD-1 interaction is selected from the group consisting of envafolimab, nivolumab, pembrolizumab, atezolizumab, avelumab, durvalumab, cemiplimab, spartalizumab, camrelizumab, sinilimab, tislelizumab, torpalimab, AMP-224, AMP-514, and combinations thereof.

Various inhibitors of MDSCs, including G-MDSCs, are known in the art. In embodiments, the inhibitor of MDSCs is selected from the group consisting of tyrosine kinase inhibitors, phosphodiesterase-5 (PDE-5) inhibitors, nitroaspirins, synthetic triterpenoids, cyclooxygenase 2 (COX2) inhibitors, arginase inhibitors, and combinations thereof. In a specific embodiment, the MDSC inhibitor is a tyrosine kinase inhibitor. In a more specific embodiment, the tyrosine kinase inhibitor is selected from the group consisting of cabozantinib, sunitinib, erlotinib, gefitinib, lapatinib, vatalanib, vamdetanib, imatinib, sorafenib, AZD0530, dasatinib, and combinations thereof. In a more specific embodiment, the tyrosine kinase inhibitor is cabozantinib or sunitinib. Other suitable inhibitors are found, for example, in Wesolowski, et al., *Myeloid derived suppressor cells—a new therapeutic target in the treatment of cancer*, J. for Immunotherapy of Cancer, 1: 10 (2013); Gupta, et al., *Small molecule tyrosine kinase inhibitors in pancreatic cancer*, Biologics 2(4): 707-15 (2008), incorporated herein by reference.

The inhibitor of PD-L1/PD-1 interaction and the inhibitor of G-MDSCs may be co-administered to the patient. Such co-administration comprises contemporaneous and sequential administration.

In another embodiment, the method further comprises administering to the patient an effective amount of a third active agent suitable for the treatment of pancreatic cancer. In embodiments, the active agent is selected from the group consisting of abraxane, afinitor, everolimus, 5-FU, capecitabine, fluoracil, gemcitabine, irinotecan liposome, olaparib, mitomycin C, paclitaxel, FOLFIRINOX, cisplatin, oxaliplatin, leucovorin, lanreotide acetate, lutetium Lu 177-dotatate, and combinations thereof.

The term "administering," as used herein, refers to any route of administering an effective amount of a therapeutic agent. In some embodiments, the administering includes, but is not limited to, oral, intravenous, subcutaneous, intramuscular, intraperitoneal, sublingual, rectal, nasal, pulmonary or inhaled, and transdermal administration. In specific embodiments, the therapeutic agent is administered intravenously or orally. In a very specific embodiment, the therapeutic agent is administered intravenously.

As used herein, the terms "sequential" or "sequentially" refer to a treatment protocol in which administration of a first therapeutic agent is followed by administration of a second therapeutic agent. Additional (third, fourth, etc.) therapeutic agents may also be administered sequentially.

As used herein, the terms "contemporaneous" or "contemporaneously" refer to administration of a first therapeutic agent and administration of a second therapeutic agent, wherein the first and second therapeutic agents are separate and are administered at substantially the same time. Additional (third, fourth, etc.) therapeutic agents may also be administered contemporaneously.

As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain an effective amount when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be effective as described herein.

In another embodiment, a method for determining whether a pancreatic cancer patient is likely to benefit from a candidate therapy is provided, comprising: providing an autologous pancreatic tumor organoid and immune cell co-culture as described herein, comprising at least one pancreatic tumor organoid cultured from the patient's pancreatic tumor cells, autologous cytotoxic T lymphocytes (CTLs) activated by dendritic cells pulsed in tumor organoid-conditioned media, and myeloid derived suppressor cells (MDSCs) differentiated from autologous peripheral blood mononuclear cells (PBMCs) cultured in tumor organoid-conditioned media; contacting the autologous pancreatic tumor organoid and immune cell co-culture with the candidate therapy; detecting one or more changes in the autologous pancreatic tumor organoid and immune cell co-culture indicative of therapeutic efficacy of the candidate therapy against the autologous pancreatic tumor organoid and immune cell co-culture; and determining that the patient is likely to benefit from the candidate therapy when the one or more changes indicative of therapeutic efficacy are detected. The one or more changes are selected from the group consisting of tumor organoid cell death, decreased population of MDSCs (including M-MDSCs and/or G-MDSCs), and CTL proliferation.

"Likely to benefit," as used herein, means the patient is more likely than not to experience partial or complete effective treatment as a result of the administered therapy. For example, if a patient is likely to benefit from a therapy, the therapy is predicted to partially or completely alleviate, ameliorate, relieve, inhibit, prevent, delay onset of, reduce severity of and/or reduce incidence of one or more symptoms or features of the patient's pancreatic cancer. In embodiments, the patient is more likely than not to experience tumor cell death or shrinkage, decreased population of MDSCs (including M-MDSCs and/or G-MDSCs), particularly within the patient's tumor microenvironment, and/or CTL proliferation.

In embodiments, the method further comprises administering an effective amount of the candidate therapy to the pancreatic cancer patient. In embodiments, the candidate therapy inhibits programmed cell death ligand 1 (PD-L1)/programmed cell death 1 (PD-1) interaction and/or depletes MDSCs. In a specific embodiment, the candidate therapy inhibits PD-L1/PD-1 interaction and depletes MDSCs, including G-MDSCs.

Methods of Screening for Pancreatic Cancer Therapies

Also provided herein are methods of screening for effective pancreatic cancer therapies, comprising: providing an autologous pancreatic tumor organoid and immune cell co-culture as described herein, comprising at least one pancreatic tumor organoid cultured from the patient's pancreatic tumor cells, autologous cytotoxic T lymphocytes (CTLs) activated by dendritic cells pulsed in tumor organoid-conditioned media, and myeloid derived suppressor cells (MDSCs) differentiated from autologous peripheral blood mononuclear cells (PBMCs) cultured in tumor organoid-conditioned media; contacting the autologous pancreatic tumor organoid and immune cell co-culture with the candidate therapy; detecting one or more changes in the autologous pancreatic tumor organoid and immune cell co-culture indicative of therapeutic efficacy of the candidate therapy against the autologous pancreatic tumor organoid and immune cell co-culture; and identifying the candidate therapy as an effective pancreatic cancer therapy when the one or more changes indicative of therapeutic efficacy are detected. In embodiments, the one or more changes are selected from the group consisting of tumor organoid cell death, decreased population of MDSCs (including M-MDSCs and/or G-MDSCs), and CTL proliferation.

In a further embodiment, the method comprises administering the identified candidate therapy to a patient in need thereof.

EXAMPLES

The following detailed methodology and materials are set forth to support and illustrate particular aspects and embodiments of the invention, and should not be construed as limiting the scope thereof.

Example 1. Materials and Methods

Mouse Orthotopic Transplants and Treatment

C57BL/6 mice purchased from Jackson Laboratories (JAX) and Taconic Farms (TAC) were orthotopically transplanted with 500,000 7940B cells derived from a primary spontaneous PDAC tumor arising in the body of the pancreas (C57BL/6) of a male transgenic $Kras^{LSL-G12D/+}$, $Trp53^{LSL-R172H/+}$, Pdx1-Cre (KPC) mouse (donated by Dr. Gregory Beatty, University of Pennsylvania). Nod scid gamma mice were orthotopically transplanted with 500-1000 pancreatic cancer organoids derived from PDAC patients.

In a separate series of experiments, 7 days post-orthotopic transplantation, C57BL/6 mice (Jackson Laboratories) were treated with gemcitabine (Selleckchem) (325 µg/mouse, i.p.) every 2 weekdays and abraxane (Selleckchem) (13 µg/mouse, i.v.) every 5 days, nivolumab (Selleckchem) (200 µg/mouse, i.p.) every 5 days, cabozantinib (cabo, Selleckchem) (780 µg/mouse, oral gavage) every weekday or a combination of 3 or 4 drugs for 7 days. Tumor tissue was analyzed for changes in weight and size using $^{18}$F-FDG PET/CT imaging. $^{18}$F-FDG PET/CT imaging was performed at the Vontz Core Imaging Laboratory at the University of Cincinnati. Following administration of $^{18}$F-FDG (6.4-7.5 MBq [174-202 µCi]) via lateral tail vein injection in anaesthetized mice, animals were awakened and returned to individual holding cages for 60 minutes. Precisely 60 minutes post-FDG injection, re-anesthetized mice were placed prone in a heated (37° C.) multimodality chamber (M2M Imaging, Cleveland, OH, USA) in the PET scanner's gantry. PET list mode data was acquired for 15 minutes, using an Inveon small-animal PET/CT/SPECT imaging system (Preclinical Solutions, Siemens Healthcare Molecular Imaging, Knoxville, TN, USA). In the same workflow, a CT image was acquired. Images were reconstructed using a three-dimensional OP-MAP algorithm (Siemens Medical Solutions USA, Inc., Malvern, PA, USA).

Generation of Mouse- and Human-Derived Pancreatic Cancer Organoids

Tumor tissue was obtained from patients undergoing surgical resection for pancreatic cancer. Mouse and human pancreatic tumors were harvested in wash buffer ((DBPS, Corning) supplemented with 1% Penicillin/Streptomycin (Corning), 1% Kanamycin Sulfate (ThermoFisher Scientific) and 0.2% Gentamicin/Amphotericin B (ThermoFisher Scientific)). Tumor tissue was then mechanically minced with razor blades and suspended in 5 mL of HBSS (Corning) supplemented with 5% FCS (Atlanta Biologicals), 1% Penicillin/Streptomycin (Corning), 1% Kanamycin Sulfate (ThermoFisher Scientific) and 0.1% Gentamicin/Amphotericin B (ThermoFisher Scientific) containing 1 mg/mL Collagenase P (Roche). Tumor tissue was digested by incubating at 37° C. for 15 mins with vortexing every 5 mins. After 15 mins, tissue fragments were analyzed under a microscope. If clusters of cells were present, the reaction was stopped with 5 mL of HBSS supplemented with 5% FCS (Atlanta Biologicals), 1% Penicillin/Streptomycin, 1% Kanamycin Sulfate and 0.1% Gentamicin/Amphotericin B. Digested tissue was rinsed in wash buffer and filtered through a 7004 filter.

Filtrate was carefully removed and centrifuged at 300×g for 5 mins. Cells were then suspended in Matrigel® (Fisher Scientific) supplemented with 1% Penicillin/Streptomycin and 1% Kanamycin Sulfate and then overlaid with organoid media. Human-derived organoids (HuTPOs) were cultured in human pancreatic media ((DMEM/F12 (ThermoFisher), 1×B27 (Thermofisher), 284 µM ascorbic acid (R&D), 20 µg/µL Insulin (R&D), 0.25 µg/µL hydrocortisone (Sigma), 100 ng/mL FGF2 (Peprotech), 100 nM ATRA (Sigma), 10 µM Y27632 (Sigma), 100 ng/mL FGF10 (Peprotech), 1% Penicillin/Streptomycin (Corning), 0.1% Gentamicin/Amphotericin B (Thermofisher), 2 mM glutamax (Fisher Scientific) and 56 µg/mL BPE (Sigma), 10% R-Spondin, and 50% Wnt conditioned media). Mouse-derived organoids were cultured in mouse pancreatic media ((DMEM/F12 (ThermoFisher), 1% Penicillin/Streptomycin (Corning), 1×B27 (Thermofisher), 1.2 5 mM N-acetyl cysteine, 10 nM gastrin (Tocris), 50 ng/mL EGF (Peprotech), 10% R-Spondin, 100 ng/mL Noggin (Peprotech), 100 FGF10 (Peprotech) and 10 mM nicotinamide).

Cytometry-Time of Flight (CyTOF)

Mouse and human pancreatic tumors were harvested in wash buffer (DBPS (Corning, 21-031-CV) supplemented with 1% Penicillin/Streptomycin (Corning, 30-002-CI), 1% Kanamycin Sulfate (ThermoFisher Scientific, 15160-054) and 0.2% Gentamicin/Amphotericin B (ThermoFisher Scientific, S1714)). Tumor tissue was then mechanically minced with razor blades and suspended in 1 mL of HBSS (Corning, 21-021-CV) supplemented with 5% FCS (Atlanta Biologicals, S12450H), 1% Penicillin/Streptomycin (Corning, 30-002-CI), 1% Kanamycin Sulfate (ThermoFisher Scientific, 15160-054) and 0.1% Gentamicin/Amphotericin B (ThermoFisher Scientific, 51714) containing 1 mg/mL Collagenase P (Roche, 11213865001). Tumor tissue was digested by incubating at 37° C. for 15 mins with vortexing every 5 mins. After 15 mins, tissue fragments were analyzed under a microscope. If single cells were present, the reaction was stopped with 5 mL of HBSS supplemented with 5% FCS (Atlanta Biologicals, S12450H), 1% Penicillin/Streptomycin, 1% Kanamycin Sulfate and 0.1% Gentamicin/Amphotericin B. Cells were rinsed in wash buffer and then suspended in 5 mL of filter buffer containing HBSS/5% FCS/1% Penicillin/Streptomycin/1% Kanamycin Sulfate/0.2% Gentamicin/Amphotericin B, filtered through a 4004 filter and centrifuged at 300×g for 5 mins.

To assess cell viability, approximately $1 \times 10^7$ cells were stained with 1 µL of (5 µM) of Cell-ID™ Cisplatin according to the manufacturer's instructions (DVS Sciences). The MaxPar® Cell Surface Staining Protocol was followed according to the manufacturer's protocol (Fluidigm, PRD012). Cells were resuspended in MaxPar® Cell Staining Buffer containing the following antibodies from Fluidigm (CD3 (170Er, 3170001C), CD4 (145Nd, 3145001C), CD8a (146Nd, 3146001C), CD14 (160Gd, 3160001C), CD16 (148Nd, 3148004B), CD27 (167Er, 3167002B), CD38 (172Yb, 3172007B), CD45ra (169Tm, 3169008C), CD163 (154Sm, 3154007B), CTLA-4 (161 Dy, 3161023B), PD-1 (174Yb, 3174020B), CD206 (168Er, 3168008B), CD44 (166Er, 3166001B), CD11b (144Nd, 3144001B), CD33 (158Gd, 3158001B), HLA-DR (143Nd, 3143013B), CD15 (149Sm, 3149026D) and CD66b (152Sm, 3152011B). Cells were resuspended in 1 mL cell intercalation solution (125 nM Cell-ID Intercalator-Ir in Maxpar Fix and Perm Buffer) for shipment overnight on ice to the University of Rochester Medical Center, New York where final washes with Maxpar water were performed according to manufacturer's instructions and the samples were run on a CyTOF machine. Data was analyzed using Premium CytoBank Software and FlowJo.

Drug Assays

To determine the ED50 drug concentrations, organoids were grown in 96 well plates and treated with various standard-of-care chemotherapeutics that the patient was treated with including FOLFIRINOX (oxaliplatin (Sigma), leucovorin (Selleckchem), irinotecan (Selleckchem) and 5-fluorouracil (Selleckchem)) or gemcitabine (Selleckchem) and Epothilone A (abraxane) (Selleckchem). Mouse-derived organoids were treated with gemcitabine and abraxane. Drug concentrations ranged from 0, 0.5, 1, 5, 10, 50, 100 and 200 µM. After 72 hours, organoid proliferation was measured by MTS Assay (Promega, G3580). The absorbance was normalized in order to scale the proliferation from 0-100% (100% being untreated organoids). Concentrations were transformed to a logarithmic scale, and a best fit non-linear dose-response curve was plotting using GraphPad Prisim Software (GraphPad Software, San Diego, CA). Organoids were treated at the ED50 drug concentrations 0 to 72 hours and the average ratio of live/dead cells were analyzed by flow cytometry (ThermoFisher), and analyzed by FlowJo.

Extraction and Culture of Murine and Human Immune Cells

Murine monocytes were isolated and cultured from bone marrow according to a published protocol (Wang, et al., *Culture and Identification of Mouse Bone Marrow-Derived Dendritic Cells and Their Capability to Induce T Lymphocyte Proliferation, Med Sci Monit* 22: 244-50 (2016)). Dendritic cells were cultured from bone marrow-derived monocytes according to published protocol (Chakrabarti, et al., *Mouse-Derived Gastric Organoid and Immune Cell Co-culture for the Study of the Tumor Microenvironment, Methods Mol Biol* 1817:157-68 (2018)). CTLs were extracted from splenocytes using the EasySep™ Mouse CD8+ T cell Isolation kit according to manufacturer's protocol (Stemcell Technologies, 19853) and cultured according to previously published studies (Chakrabarti, et al.).

Whole blood was collected from PDAC patient blood. Sepmate™ tubes (Stemcell Technologies) containing Lymphoprep™ (Stemcell Technologies) were used to separate out red blood cells and platelets according to manufacturer's protocol. The resulting peripheral blood mononuclear cells (PBMCs) were cultured in human monocyte media, human dendritic cell media, or put through the negative selection EasySep Human CD8+ T cell Enrichment Kit (Stemcell). PBMCs were matured into human dendritic cells using a modified published protocol (Nair, et al., *Isolation and generation of human dendritic cells, Curr. Prot. Immunol.* Ch. 7, Unit 7: 32 (2012)) consisting of AIM V medium supplemented with 800 U/m GM-CSF, 500 U/ml IL-4 and 1% penicillin/streptomycin and 10% human serum albumin. Dendritic cells were then matured 72 hours after culture using maturation media consisting of AIM V medium, 800 U/ml GM-CSF, 500 U/ml IL-4, 1% penicillin/streptomycin, 10 ng/ml TNFα, 10 ng/ml IL-1β, 10 ng/ml IL-6, 1 μg/ml $PGE_2$, amphotericin/gentamycin, kanamycin. Dendritic cells were kept in maturation media for 16 hours. Human CD8+ T Cells extracted from PBMCs were cultured for 16 hours using a protocol adapted from a published protocol (Lewis, et al., *A reproducible method for the expansion of mouse CD8+ T lymphocytes, J. Immunol. Methods* 417:134-38 (2015)) and media consisting of RPMI medium, 10% Human serum albumin, 1% penicillin/streptomycin, β-Mercaptoethanol, ITS (1:1000), IL-2 (10 ng/ml) and IL-7 (10 ng/ml). MDSCs were cultured in 50% MDSC culture media (AIM V medium, IL-1β (10 ng/ml), IL-6 (10 ng/ml), $PGE_2$ (1 μg/ml), TGFα1 (2 ng/ml), TNFα (10 ng/ml), GM-CSF (10 ng/ml), VEGF (10 ng/ml), 1% penicillin/streptomycin, amphotericin/gentamycin) and 50% tumor organoid conditioned media for 7 days, removing half of the media and replacing with fresh media/conditioned media every 48 hours.

Human- and Mouse-Derived Pancreatic Cancer/Immune Cell Co-Cultures

After maturation, dendritic cells were pulsed with either mouse- or human-derived pancreatic cancer organoid tumor conditioned media for 2 hours by replacing the maturation media with 50% organoid conditioned media. Pulsed dendritic cells were then co-cultured with murine- or human-derived CD8+ cytotoxic T lymphocytes (CTLs) at a ratio of 1:5 (DCs:CTLs) for 72 hours in DC/CTL co-culture media (RPMI, 10% Human Serum Albumin, 1% penicillin/streptomycin). 72 hours after co-cultures, CTLs were harvested and used in co-culture with either human- or mouse-derived pancreatic cancer organoids and monocytes. Human T cells were extracted from the CD8+ T Cell/dendritic cell co-culture using the EasySep™ Human CD8 Positive Selection Kit II (Stemcell Technologies) following manufacture's protocol. Murine T cells were extracted from the CD8+ T Cell/dendritic cell co-culture using the EasySep Murine CD8 Positive Selection Kit II (Stemcell Technologies) following manufacture's protocol. Organoids were harvested from the Matrigel® using cold DMEM/F12 and centrifuged at 400×g for 5 mins at 4° C. Organoids and CTLs and/or MDSCs were resuspended in Matrigel®. Human and mouse co-cultures were cultured in human and murine pancreatic media respectively (Huch, et al., *Unlimited in vitro expansion of adult bi-potent pancreas progenitors through the Lgr5/R-spondin axis, EMBO J.* 32: 2708-21 (2013)). 72 hours after co-culture organoids, CTLs and MDSCs were analyzed by immunofluorescence, flow cytometry, and qRT-PCR.

Immunofluorescence and Immunohistochemistry

Organoids were fixed in 3.7% formaldehyde, permeabilized with 0.5% Triton X-100 for 20 mins at room temperature and blocked with 2% normal donkey serum (Jackson Immunology) for 1 hour at room temperature. Human-derived cultures were immunostained using antibodies specific for HNF-1β (Novus Biologicals, Rabbit, 1:50), Sox 9 (Novus Biologicals, mouse, 1:250) and CK19 (R&D, sheep, 1:80), PD-L1 (Novus Biologicals, rabbit, 1:100), CD11b (Novus Biologicals, rat, 1:100), CD8a (MAB1509, R&D, mouse, 1:60) and/or E-cadherin (R&D, Goat, 1:400). Murine pancreatic organoid cultures were immunostained with antibodies specific for CD11b (Novus Biologicals, rabbit, 1:100), CD8a (Novus Biologicals, rat, 1:100) and/or E-cadherin. Pancreatic organoids were then stained with a 1:100 dilution of secondary antibodies (647 donkey anti-sheep, 647 donkey anti-goat, 594 donkey anti-mouse and 488 donkey anti-rabbit and 488 donkey anti-rat) and counter stained with (Hoechst, 10 μg/ml, Invitrogen) for 1 hour at room temperature. Organoids were visualized using the Zeiss LSM710.

Murine pancreatic tumor tissue was fixed in 4% paraformaldehyde, embedded in paraffin and sectioned (5 microns). After deparaffinization and antigen retrieval (Antigen Unmasking Solution, Vector Laboratories, Burlingame, CA), endogenous peroxidase activity was blocked using 0.3% hydrogen peroxide/methanol for 20 minutes. Slides were then blocked with 20% goat serum (ImmPRESS™ HRP Anti-Rabbit IgG reagent kit, Vector) for 20 mins at room temperature, and then incubated with a 1:2000 dilution of an anti-PCNA antibody (Novus, rabbit) antibody overnight at 4° C. Sections were then incubated with anti-rabbit ImmPRESS Ig (Vector Lab) for 30 minutes at room temperature. The color of PCNA was then developed with peroxidase substrate solution from the ImmPACT DAB Peroxidase (HRP) Substrate Kit (Vector Lab). Slides were further blocked with 20% goat serum (ImmPRESS™ HRP Anti-Rat IgG reagent kit, Vector Lab) for 20 mins at room temperature, followed by incubation with a 1:100 dilution of anti-CD8 antibody (Novus Biologicals, rat) overnight at 4° C., and then anti-rat ImmPRESS Ig (Vector Lab) for 30 minutes at room temperature. Finally, the color of CD8 was developed with VIP from the ImmPACT VIP Peroxidase (HRP) substrate kit (Vector Lab). The slides were mounted with Permount (Fisher Scientific Company) and visualized by light microscopy. Morphometric analysis of the number of CD8+CTLs was analyzed using Aperio eSlide Manager software.

Flow Cytometry

Organoids were dissociated from cultures using Accutase (Fisher Scientific) and cell viability analyzed using the LIVE/DEAD Viability/Cytotoxicity Kit. Organoid and immune cell co-cultures were harvested and suspended in 1:1000 dilution of the zombie red cocktail (BioLegend) and 1:1000 dilution of the calcein violet cocktail (BioLegend). The cells were incubated in this cocktail for 20 mins at room temperature. The cells were then washed with 1 mL of 5% BSA at 300 g for 5 mins and stained with anti-PD-L1 (human, 1:100; mouse 1:100), anti-CD8 (human, 1:100; mouse, 1:100) for 15 mins at room temperature (all obtained from BioLegend). The cell suspension was then incubated at room temperature for 15 minutes with 100 μL of Reagent A (Thermofisher), washed and analyzed.

CTLs and dendritic cells were analyzed using antibodies specific for anti-CD8 and anti-PD-1, anti-IL2 and anti-IFN-γ (mouse and human, all obtained from BioLegend). Myeloid cells were harvested in cell dissociation buffer (ThermoFisher Scientific). Cells were collected and centrifuged at 300 g for 5 mins. Supernatant was discarded, and cells were suspended in 100 μL of a 1:1000 dilution of the zombie red cocktail (BioLegend) and incubated at room temperature for 20 mins. Human MDSCs were stained using antibodies specific for CD33, HLA-DR, CD16, CD14, CD11b and CD66b (all obtained from BioLegend). Mouse MDSCs were stained using antibodies specific for CD11b, Ly6G, Ly6C, and CD11c (all obtained from BioLegend). Samples were run on the CANTO 3 and analyzed by FlowJo data analysis.
Statistical Analysis Data are expressed as a mean value +/−standard error. Analysis was done using a Student's T Test, One Way or Two Way ANOVA to determine the differences between groups. Statistical significance was determined when $p<0.05$.

Example 2. Higher Granulocytic MDCS Infiltration Correlated with Larger Tumors in JAX Mice Genetically similar C57BL/6 mice purchased from two different mouse facilitates, Jackson Laboratory (JAX) and Taconic Farms (TAC), Have been shown to exhibit differences in melanoma growth rate and anti-PD-L1 efficacy related to anti-tumor immunity. In the present studies, JAX and TAC mice were used to identify whether there was a correlation between tumor growth and the percentage of infiltrating MDSCs within the tissue (FIGS. 1A-1H). JAX and TAC mice were orthotopically transplanted with syngeneic 7940b PDAC cells derived from a primary spontaneous PDAC tumor arising in the body of the pancreas (C57BL/6) of a male transgenic $Kras^{LSL-G12D/+}$, $Trp53^{LSL-R172H/+}$, Pdx1-Cre (KPC) mouse. Fourteen days post-orthotopic transplantation, JAX mice exhibited significantly greater tumor weights when compared to TAC mice (FIG. 1A). Due to this observation, JAX mice were selected as a model for aggressive PDAC and TAC mice as a model for slow-growing PDAC. Tumors extracted from JAX mice had a significantly greater percentage of infiltrating granulocytic MDSCs (G-MDSCs) compared to tumors extracted from TAC mice (FIG. 1B). Tumors extracted from TAC mice had significantly greater monocytic MDSCs (M-MDSCs) within the tumor tissue compared to JAX mice. There was no significant difference in CD8+PD-1 expression between the two animal groups (FIG. 1B). This discordance in M-MDSC and G-MDSC infiltration is also observed in human patients (Gabrilovich, et al., *Cancer Cell* (2017), Khaled, et al., *J Immunology Res* (2014)).

Figure 1F:
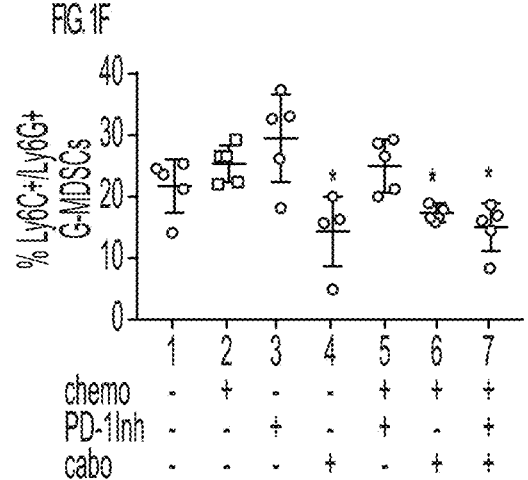
Figure 1G:
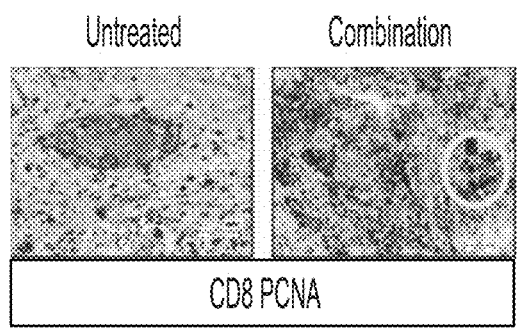
Figure 1H:
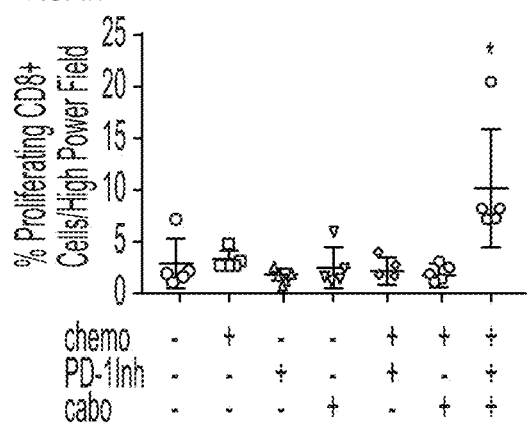
Figure 2A:
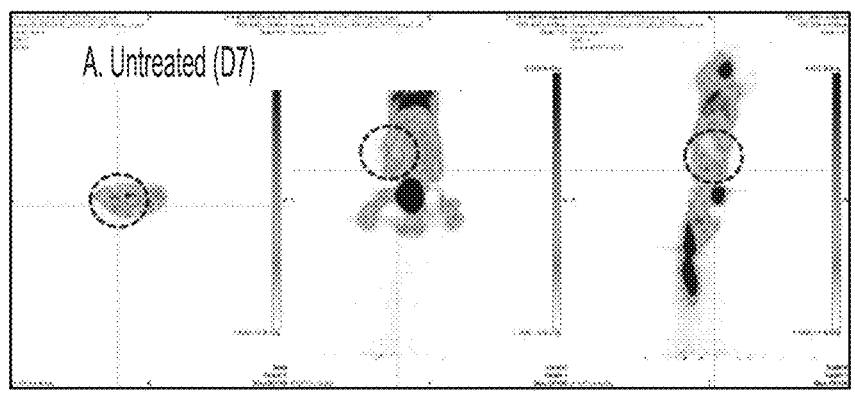
Figure 2B:
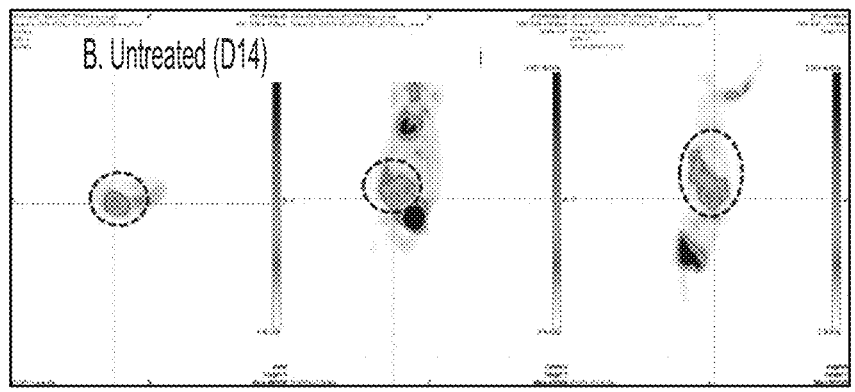
Figure 2C:
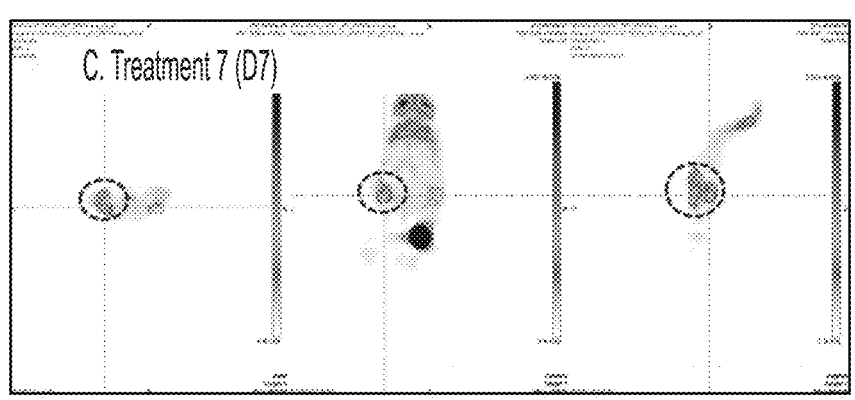
Figure 2D:
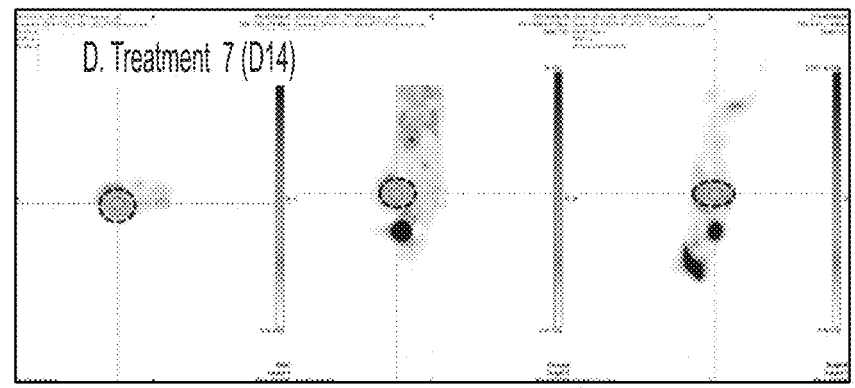

The present investigators sought to further investigate the effects of M-MDSCs and G-MDSCs on chemotherapy and anti-PD1 therapy. In a separate series of experiments, C57BL/6 JAX mice were orthotopically transplanted with syngeneic 7940b PDAC cells. After 7 days JAX mice were treated with chemotherapeutics (gemcitabine+epothilone A), nivolumab (PD-1 neutralizing antibody, verified for both murine and human use), cabozantinib (cabo) (tyrosine kinase inhibitor known to deplete MDSCs) or a combination of two or three of these drugs for a further 7 days post-orthotopic transplantation. Mice treated with a combination of gemcitabine/epothilone A, nivolumab, and cabo exhibited significantly decreased tumor weights (FIG. 1C), approximately 50% PD-L1-expressing cell death (FIG. 1D) and significantly decreased infiltrating G-MDSCs (FIGS. 1E, 1F). Decreased tumor weights in the combination treated mice correlated with increased CTL proliferation within the tumor tissue as analyzed and quantified by immunohistochemistry (FIGS. 1G, 1H). While tumor sizes grew in untreated controls between day 7 (D7) (FIGS. 2A, 2E) and day 14 (D14) (FIGS. 2B, 2E), tumor size decreased or remained unchanged in the combination treatment group (FIGS. 2C, 2D, 2E). Collectively, these data suggest that infiltrating G-MDSCs within the pancreatic tumor microenvironment contribute to increased growth of pancreatic ductal adenocarcinoma.

Figure 8A:
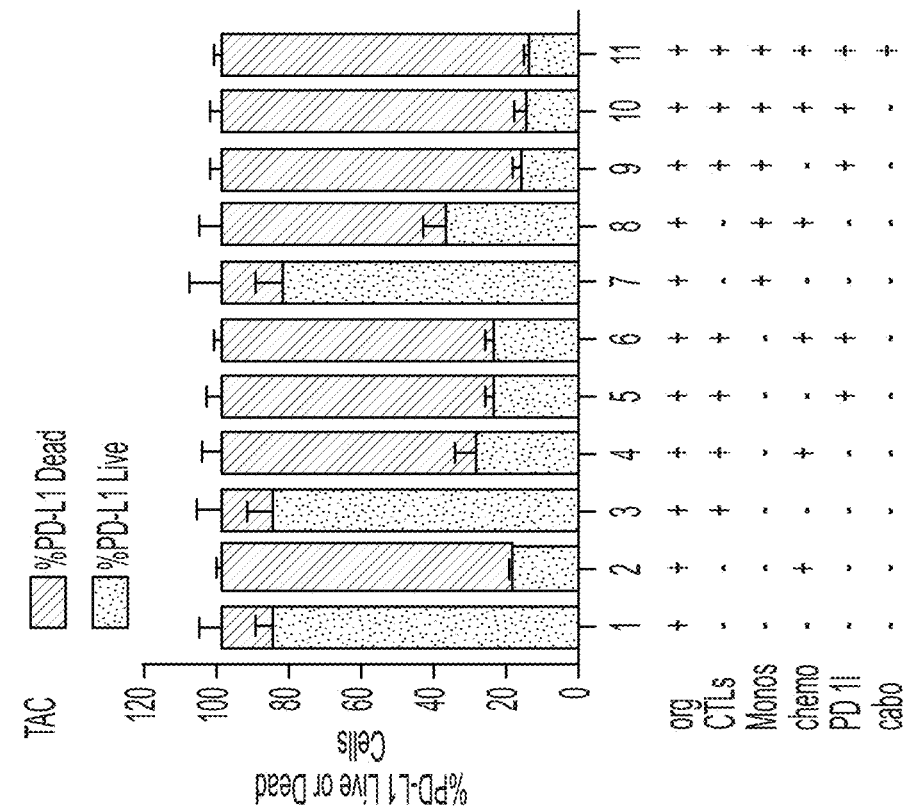
Figure 8B:
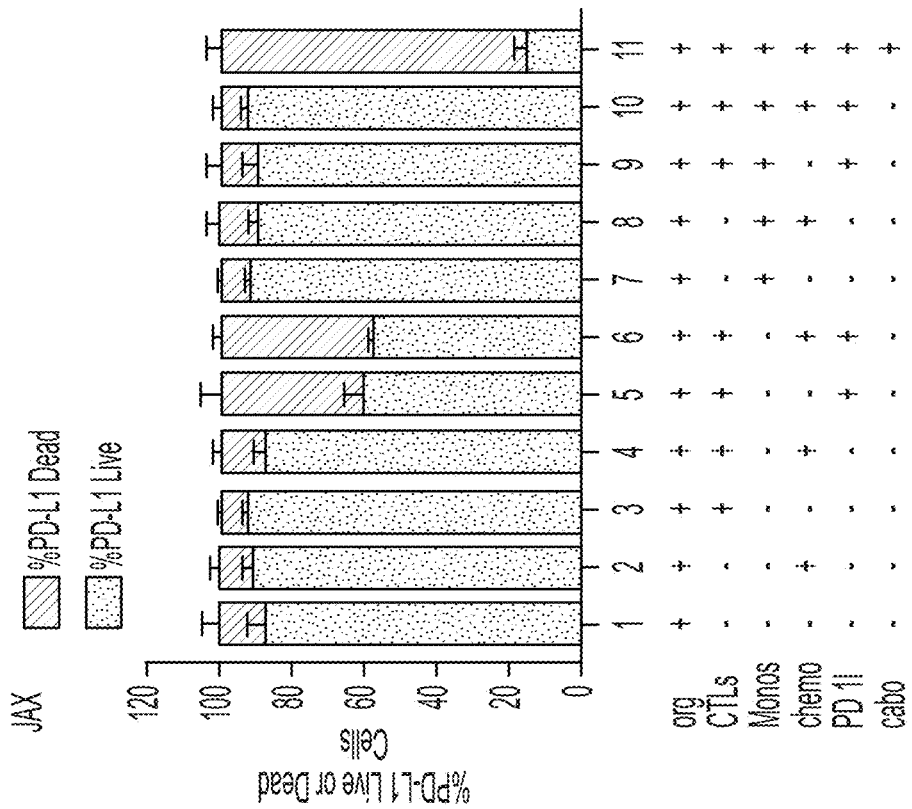
Figure 8C:
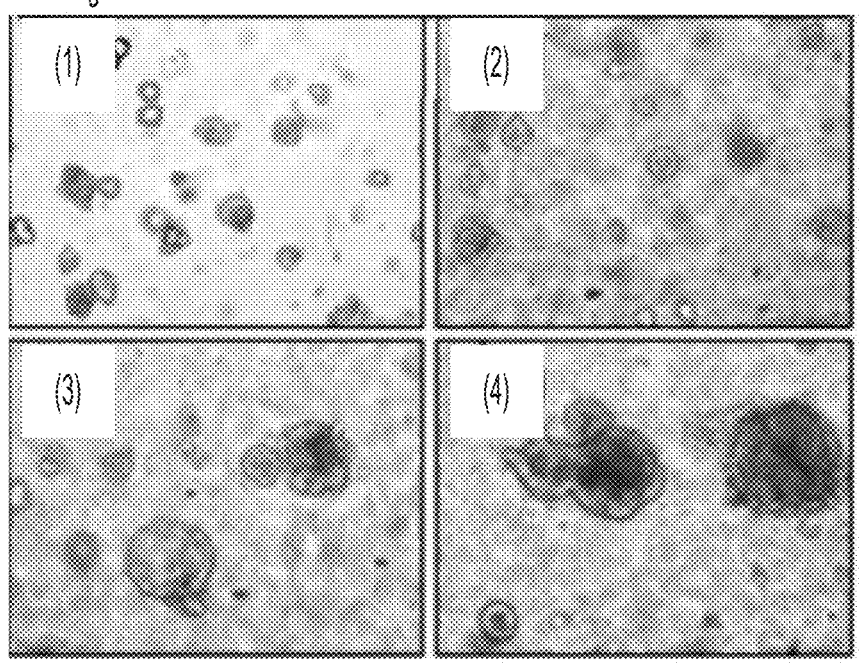
Figure 8E:
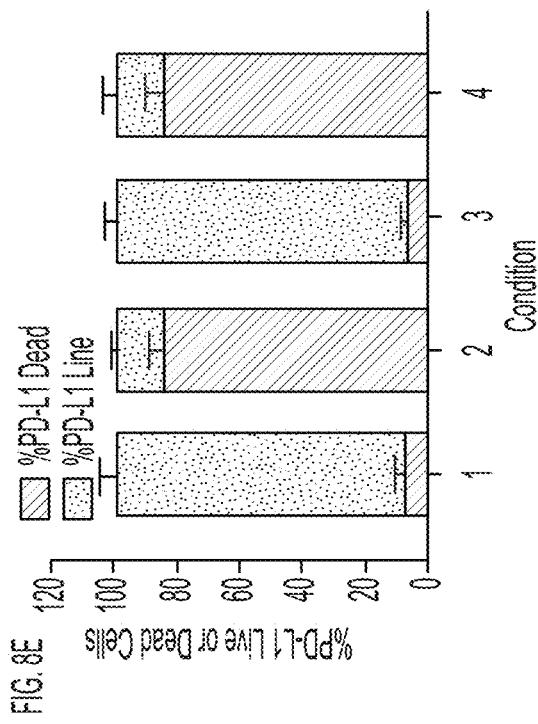
Figure 8D:
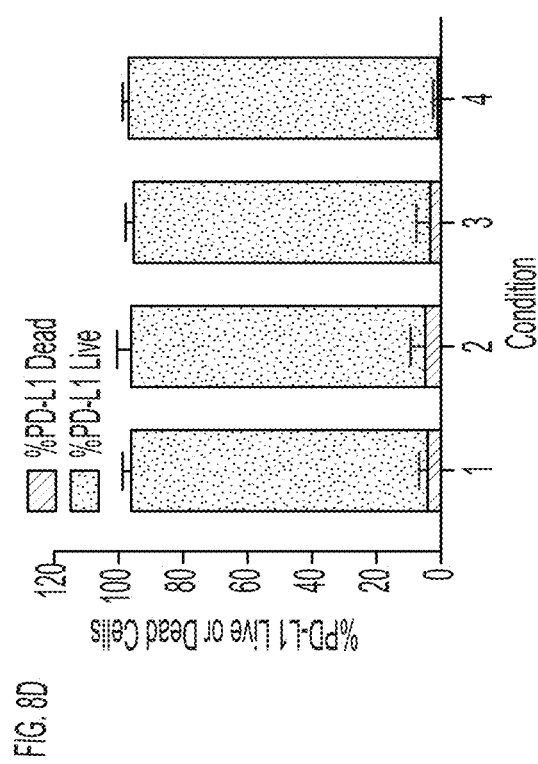
Figure 8F:
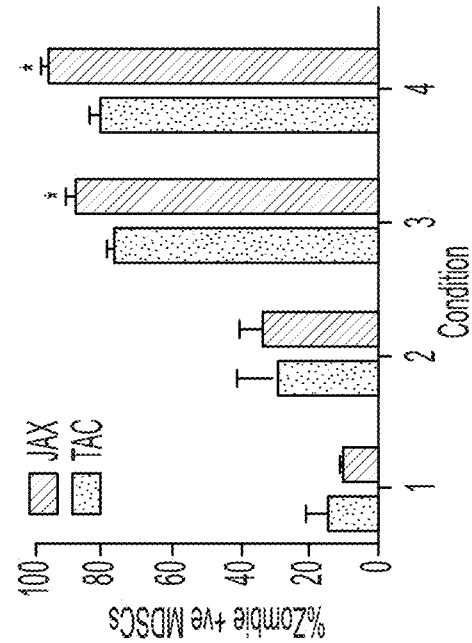

Example 3. JAX-Derived Organoids Polarize Monocytes to a G-MDSC Phenotype, Yet TAC-Derived Organoids Polarize Monocytes to an M-MDSC Phenotype JAX and TAC mice were orthotopically transplanted with syngeneic 7940b PDAC cells derived from a primary spontaneous PDAC tumor arising in the body of the pancreas (C57BL/6) of a male transgenic $Kras^{LSL-G12D/+}$, $Trp53^{LSL-R172H/+}$, Pdx1-Cre (KPC) mouse. Fourteen days post-orthotopic transplantation, JAX and TAC mice were euthanized and PDAC tumors, bone marrow, and spleens were harvested to derive murine PDAC organoids and culture autologous immune cells. Monocytes were cultured from bone marrow, and dendritic cells were differentiated from monocytes. Cytotoxic T cells (CTLs) were extracted from splenocytes using the STEMCELL Mouse CD8+ T cell Isolation kit (Stemcell Technologies). PDAC organoids were derived from both JAX and TAC PDAC tumors. Organoids derived from JAX or TAX mouse pancreatic cancer tissue (FIGS. 3A, 3B) expressed lineage markers of the pancreas including HNF-1β and CK19 (FIG. 3C). Monocytes from TAC mice that were exposed to autologous organoid conditioned media differentiated into M-MDSCs (FIG. 8H). However, JAX mouse-derived monocytes pulsed with autologous organoid conditioned media drove differentiation towards a G-MDSC phenotype (FIG. 8H). Autologous organoid/MDSCs co-cultures derived from JAX and TAC mice were treated with either chemotherapy, cabo or a combination of the two (FIGS. 8C, 8D, 8E). Treatment with either cabo, chemotherapy, or both did not significantly induce PD-L1 expressing cell death from either JAX or TAC mice (condition 3, FIGS. 8D, 8E). However, flow cytometric analysis demonstrated a significant decrease in viable MDSCs in response to cabo treatment within both JAX and TAC-derived co-cultures (FIG. 8F). Dendritic cells derived from JAX or TAC mice were pulsed with conditioned media from organoids derived from the same JAX and TAC mice. Flow cytometric analysis also demonstrated that prior to co-culture with autologous PDAC organoids there was a significant activation of CTLs from either JAX or TAC mice following co-culture with autologous dendritic cells (FIG. 8G). FIG. 8I are dose response curves of organoids derived from either JAX or TAC mice treated with gemcitabine and epothilone A (abraxane), which were used to calculate ED50 drug concentrations used in organoid-immune cell co-cultures.

Collectively, these in vivo and in vitro studies in the PDAC JAX and TAC orthotopic mouse models demonstrate that MDSCs contribute to tumor aggressiveness and growth, suppression of CD8+ T cell proliferation and effector function, leading to disruption of the efficacy of checkpoint inhibition.

Figure 3F:
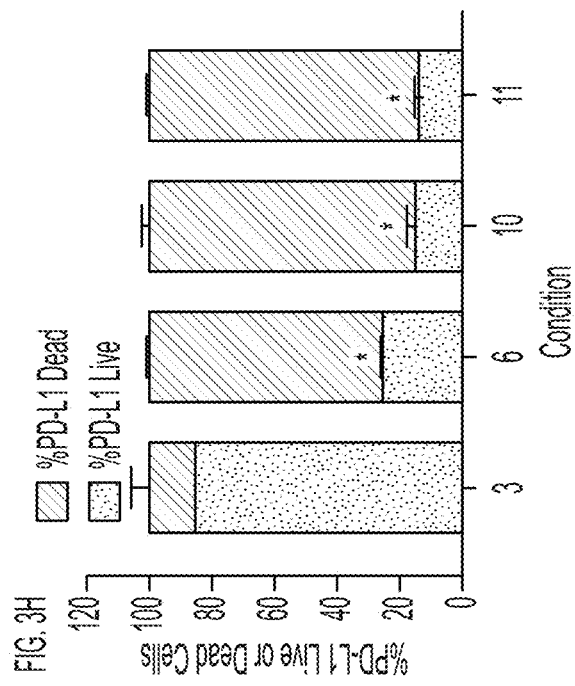
Figure 3G:
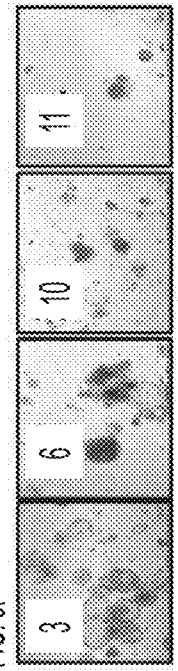
Figure 3H:
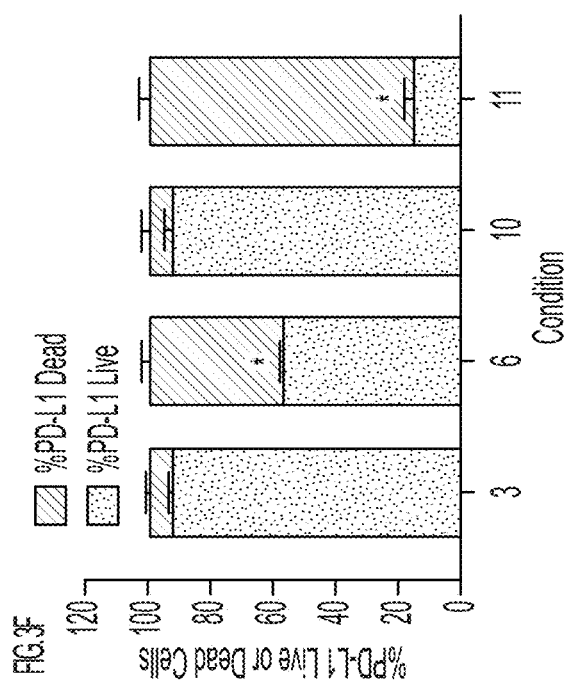
Figure 3I:
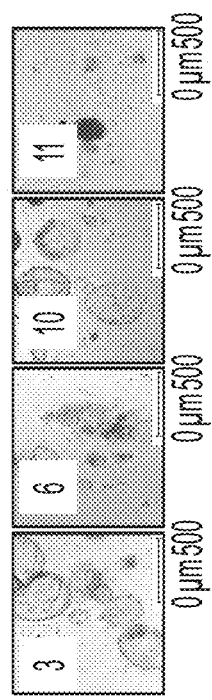

Example 4. MDCSs Disrupt the Efficacy of Checkpoint Inhibition in JAX-Derived Organoid/Immune Cell Co-Culture To investigate whether MDSCs disrupt the efficacy of checkpoint inhibition in PDAC tumor survival, a mouse-derived pancreatic cancer organoid/CTL/MDSC co-culture was developed. CTLs were extracted from co-culture with autologous dendritic cells after 72 hours using the STEMCELL mouse CD8+ T cell positive selection kit (Stemcell Technologies) (FIG. 3D). Autologous JAX or TAC PDAC organoids, CTLs and monocytes were co-cultured for 72 hours. When autologous organoid/CTL co-cultures derived from JAX mice were treated with nivolumab (PD-1Inh) and gemcitabine/epothilone A, investigators observed approximately 62% PD-L1 expressing PDAC cell death (condition 6, FIGS. 3E, 3F, 3G). Importantly, when monocytes, previously shown to differentiate to G-MDSCs in the presence of JAX-derived organoid conditioned media were added to this JAX-derived co-culture of organoids and CTLs, PD-L1 expressing PDAC cell death was inhibited (condition 10, FIGS. 3E, 3F, 3G). The addition of cabo to the JAX-derived autologous organoid/CTL/MDSC co-culture both depleted MDSCs from culture and maximized the efficacy of checkpoint inhibition to induce PD-L1 expressing cancer organoid death (condition 11, FIGS. 3E, 3F, 3G). TAC-derived organoid/CTL co-cultures were sensitive to chemotherapy and nivolumab treatment (condition 6, FIGS. 3H, 3I, 3E), whereby the addition of monocytes, previously shown to differentiate into M-MDSCs in the presence of TAC-derived PDAC organoid conditioned media (FIG. 8H), did not affect PD-L1 expressing organoid death (condition 10, FIGS. 3H, 3I, 3E). Representative images of JAX and TAC mouse-derived organoid/CTL/MDSC co-cultures under conditions 3, 6, 10 and 11 are shown in FIGS. 3G and I respectively. FIG. 3E is a schematic diagram summarizing the composition and treatments of co-culture conditions 3, 6, 10 and 11.

Figure 3K:
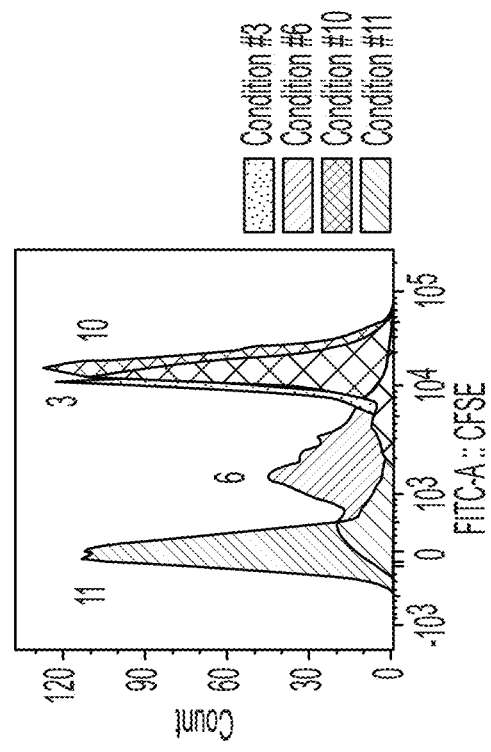
Figure 3J:
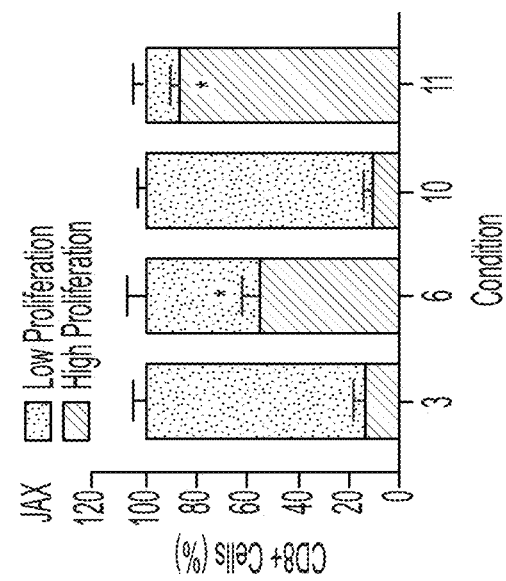
Figure 3M:
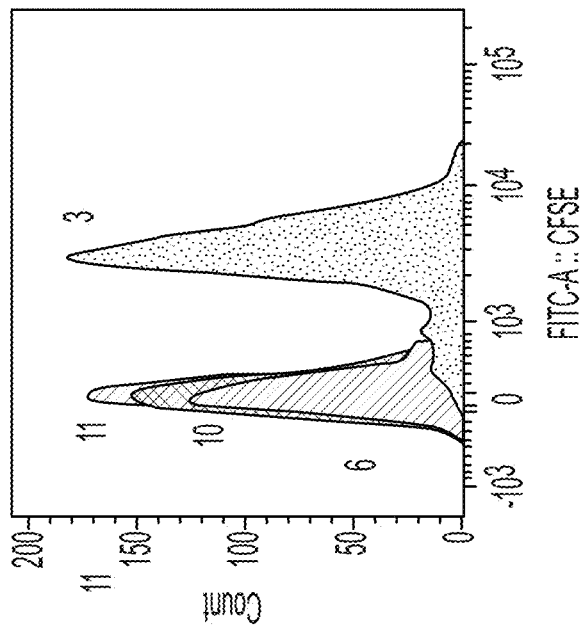
Figure 3L:
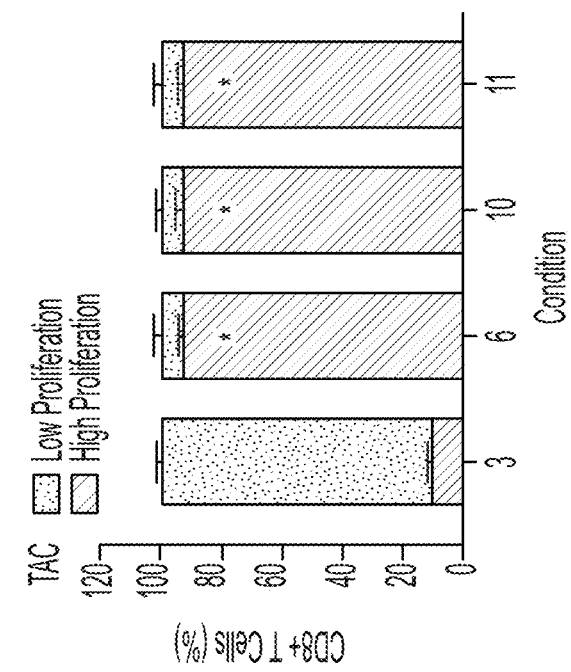

To identify the impact of MDSCs on CD8+ T cell proliferation, an in vitro assay based on cell CFSE uptake was performed. CD8+ T cells within cultures of JAX mouse-derived pancreatic cancer organoids without autologous MDSCs exhibited moderate proliferation in response to nivolumab (PD-1Inh) and chemotherapy (condition 6, FIGS. 3J, 3K). This proliferative response was diminished with the introduction of MDSCs within the co-culture (condition 10, FIGS. 3J, 3K). Interestingly, combinatorial treatment with chemotherapy, nivolumab (PD-1Inh) and cabo, resulted in the induction of CD8+ T cell proliferation (condition 11, FIGS. 3J, 3K). CD8+ T cell proliferation was significantly induced whether TAC-derived PDAC organoid/CTL/MDSC autologous co-cultures were treated with chemotherapy and nivolumab (PD-1Inh) or the combination therapy of chemotherapy, nivolumab (PD-1Inh) and cabo. (FIGS. 3L, 3M). All experimental co-culture conditions are shown in FIGS. 8A and 8B.

Figure 4A:
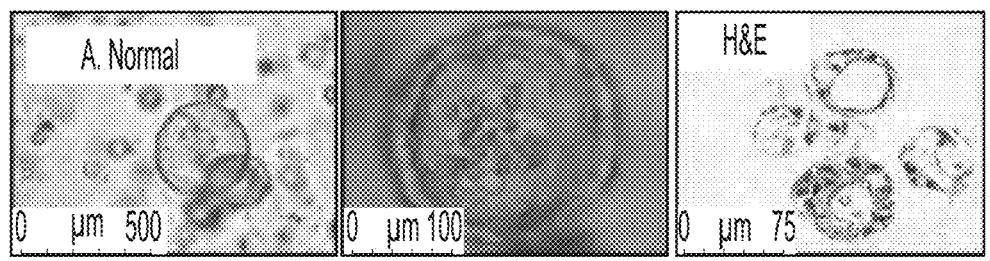
FIGS. 4A-4O. Generation, characterization, and orthotopic transplantation of human-derived PDAC organoids. Light micrographs and H&E staining of (FIG. 4A) normal and (FIG. 4B) PDAC organoids. Immunofluorescence staining of pancreatic organoids for expression of (FIG. 4C) HNF1β and cytokeratin 19 (CK19) or (FIG. 4D) HNF1β and SOX9. Nuclei stain shown by Hoechst.
Figure 4B:
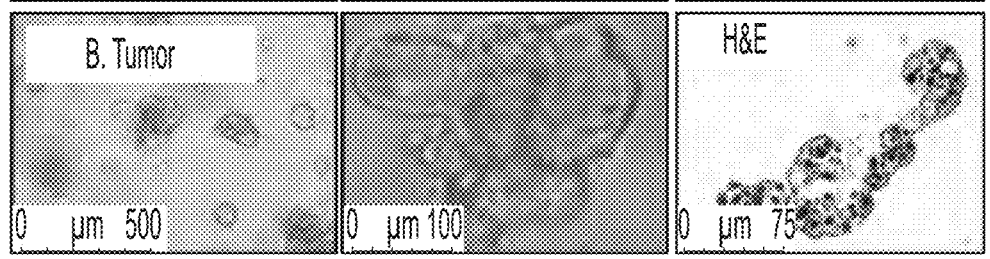
(FIG. 4E, FIG. 4F) Development of pancreatic tumors in NSG mice transplanted with PDAC organoids. H&E stains of (FIG. 4G, FIG. 4H) pancreas, (FIG. 4J, FIG. 4K) spleen, and (FIG. 4M, FIG. 4N) muscle. Immunofluorescence stain of human-specific histone of PDAC lesions within (FIG. 4I) pancreas, (FIG. 4L) spleen, and (FIG. 4O) muscle. Nuclei stain shown by Hoechst.
Figure 4C:
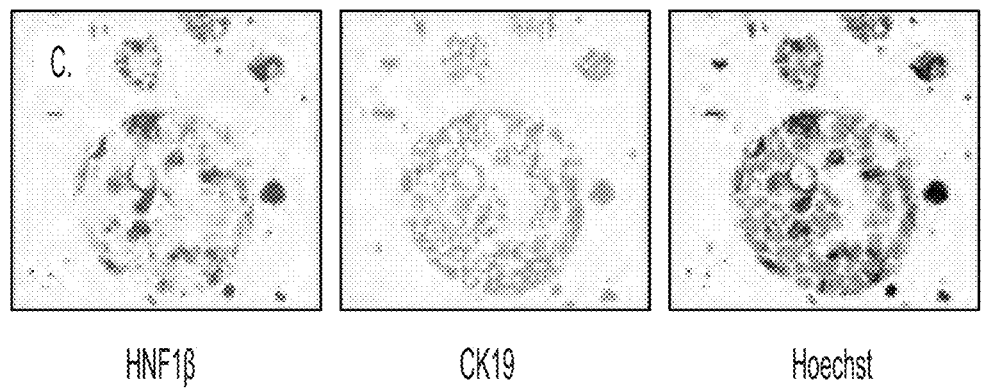
Figure 4D:
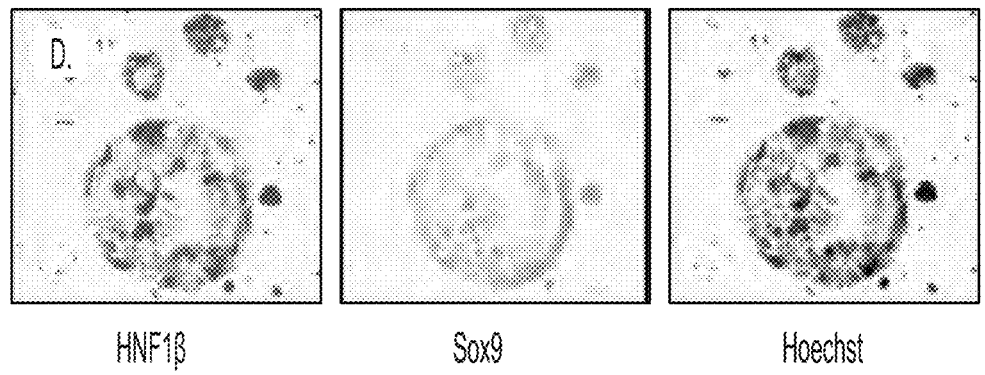

Example 5. Generation of PDAC Patient-Derived Organoids and Orthotopic Transplantation FIGS. 4A and 4B represent an example of one normal and one tumor organoid line derived from a pancreatic cancer patient with grade (3) cancer. This clearly demonstrated morphological differences between normal and tumor organoid lines. While organoids derived from normal pancreatic tissue exhibit a spherical morphology lined with ductal epithelium (FIG. 4A), PDAC organoids appeared lobular and irregular (FIG. 4B). Both normal and tumor human-derived pancreatic organoids expressed lineage markers of the pancreas including HNF-1β, CK19 and SOX9 (FIGS. 4C, 4D). Orthotopic transplantation of the human-derived PDAC organoids into Nod scid gamma (NSG) mice resulted in the development of PDAC four weeks post-engraftment (FIGS. 4E-4O). Importantly, mice transplanted with these organoids exhibited lesions in the spleen and skeletal muscle of the same mouse, mimicking early stage metastasis in human patients as confirmed by a board certified pathologist (FIGS. 4G-4O). It was confirmed that these lesions were derived from the patient's organoids by using a human-specific antibody against histone (FIGS. 4I, 4L, 4O).

Example 6. Response to Standard-of-Care Chemotherapy does not Reflect the Patient's Progression Free Survival When organoids derived from a patient were treated with the same chemotherapeutics that the patient was treated with, the response corresponded to the patient tumor's response to the same chemotherapy (FIGS. 5A, 5B). For example, organoids derived from tumor tissue of patients that exhibited an almost complete tumor response (grade 0-1, P11T) to chemotherapy (FIG. 5A) had a near complete response to that same chemotherapy, be that FOLFIRINOX or gemcitabine/epothilone A (FIG. 5B). However, organoids derived from patients that had a poor response to chemotherapy (grade 3, P10T, P26T, P28T) (FIG. 5A) did not respond well to that same chemotherapy (FIG. 5B). Importantly, patient response to chemotherapeutics was a poor indicator of disease prognosis; all cell differentiation and invasion was analyzed by a board certified pathologist (FIG. 5C). For example, organoids derived from patient P11T responded almost completely to chemotherapy in vitro (FIG. 5B). However, the patient had recurrent disease less than a year after treatment despite having a complete response to neoadjuvant chemotherapy (P11T). In contrast, organoids derived from patients P10T, P17T and P26T, did not respond to completely to chemotherapy in vitro (FIG. 5B), but these patients had an overall progression free survival based on staging (FIG. 5C).

Figure 6A:
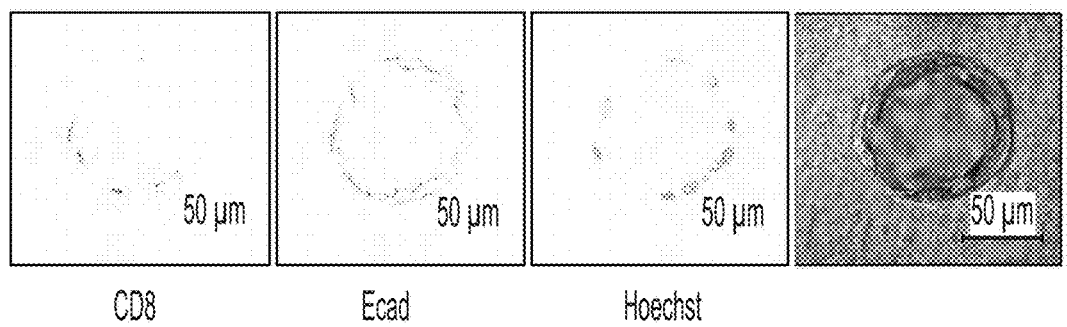
Figure 6B:
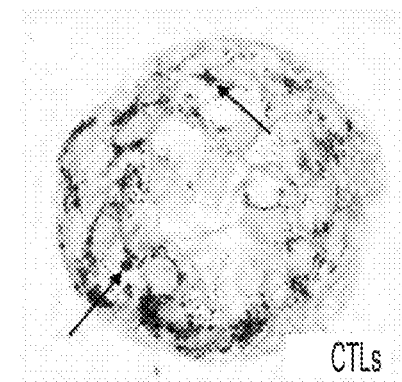
Figure 6C:
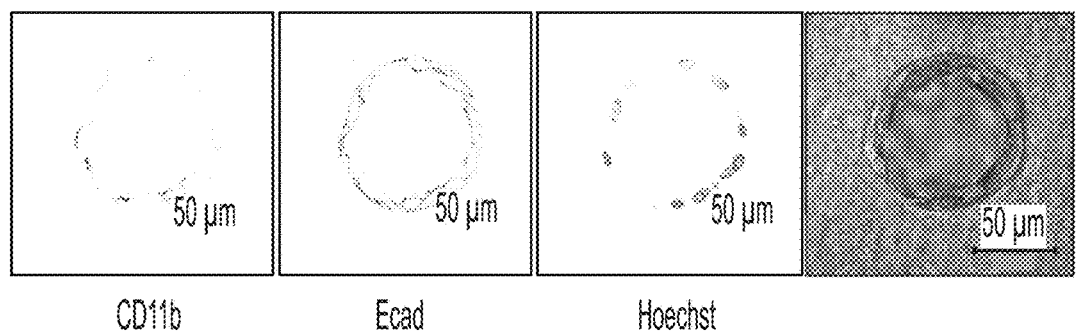

A PDAC patient-derived autologous organoid/immune cell co-culture was established (FIG. 6). CTLs were activated following a 72 hour co-culture with autologous dendritic cells that had been pulsed with the conditioned media from autologous patient-derived PDAC organoids. Following this co-culture, CTLs were extracted from dendritic cells and co-cultured with either autologous patient-derived PDAC organoids alone or with autologous monocytes. Monocytes were cultured from whole blood. Immunofluorescence showed the direct contact between CTLs and PDAC organoids (FIG. 6A), and the presence of MDSCs (FIG. 6C) in co-culture. FIGS. 6E-6G is an example of an organoid co-culture of the patient's own autologous CTLs. While organoid apoptosis was not observed in the culture with CTLs and organoids alone (FIG. 6F) compared to organoids alone (FIG. 6E), cultures depleted of MDSCs and treated with nivolumab resulted in cell death (FIG. 6G). Organoid/immune cell co-cultures from patients were grouped into advanced and early stage tumors, based on TMN grade. All organoid lines selected for subsequent co-culture experiments expressed PD-L1 (FIGS. 9A-9G).

Figure 7A:
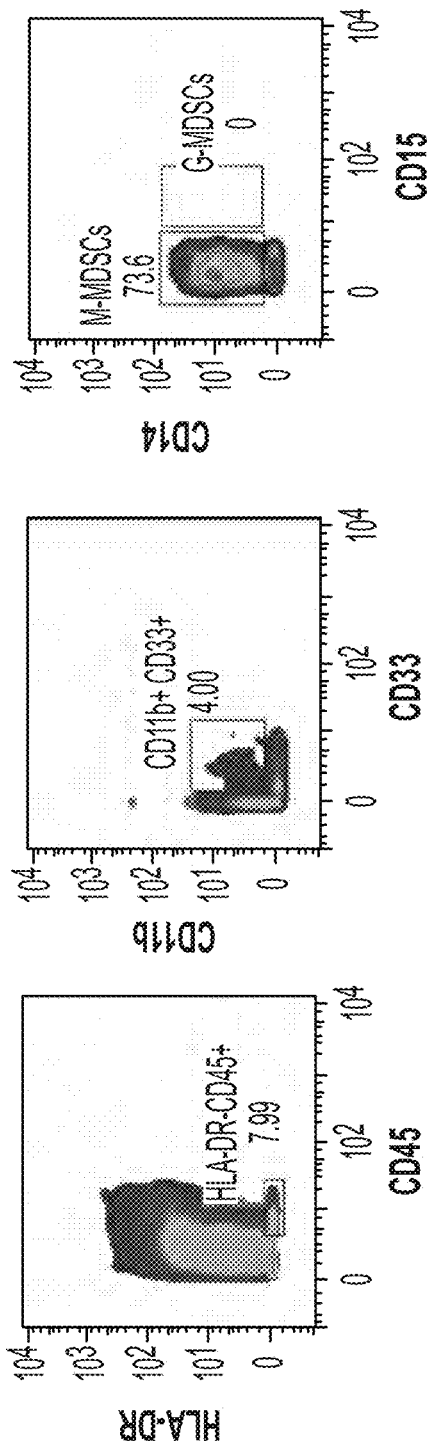
Figure 7B:
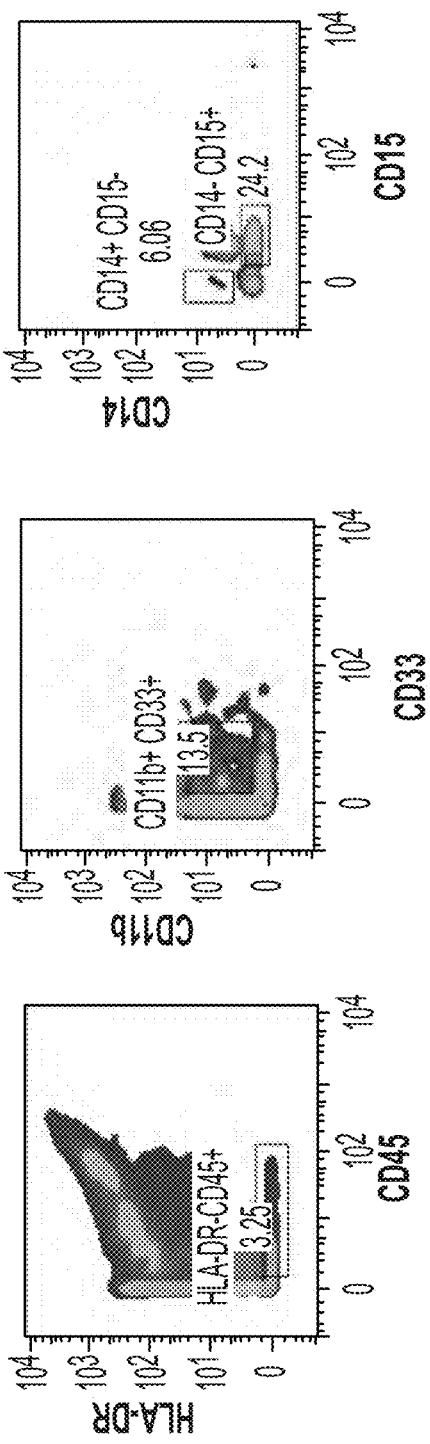
Figure 7D:
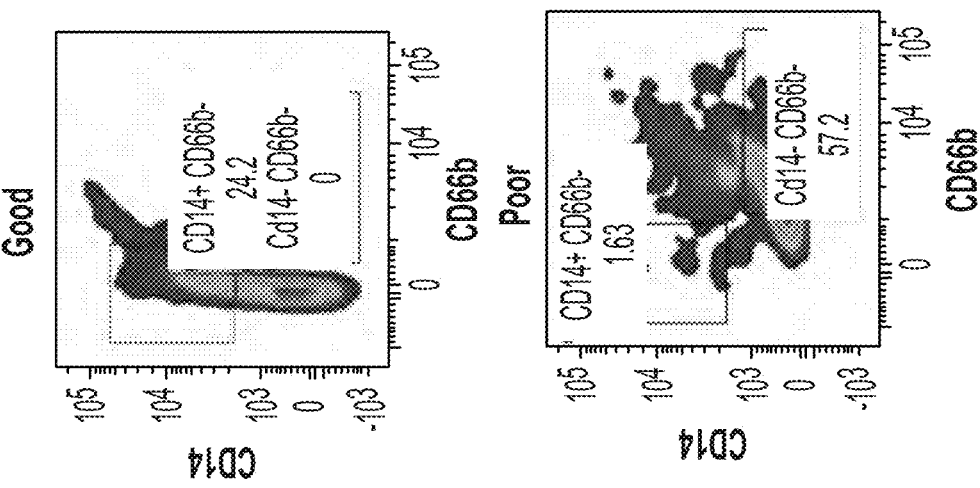

Example 7. Depletion of MDSCs from Organoid/Immune Cell Co-Cultures Derived from Patients with Advanced Stage PDAC Maximizes the Effect of Chemo- and Immunotherapy In patients with an advanced stage tumors, such as patient P28T, there was a statistically significant increase in the infiltration of G-MDSCs (CD45+HLA-DR−CD33+CD11b+CD14−, CD15+) within the tumor tissue (FIGS. 7B, 7C) compared to that of a patient with an early stage tumor (P10T, FIGS. 7A, 7C). Similarly, flow cytometric characterization of monocytes co-cultured with organoids derived from patients with an early stage tumor revealed a significantly higher M-MDSC phenotype (FIG. 7D). However, monocytes co-cultured with organoids derived from patients with an advanced stage tumor exhibited a significantly higher G-MDSC phenotype (FIG. 7E).

Figure 10A:
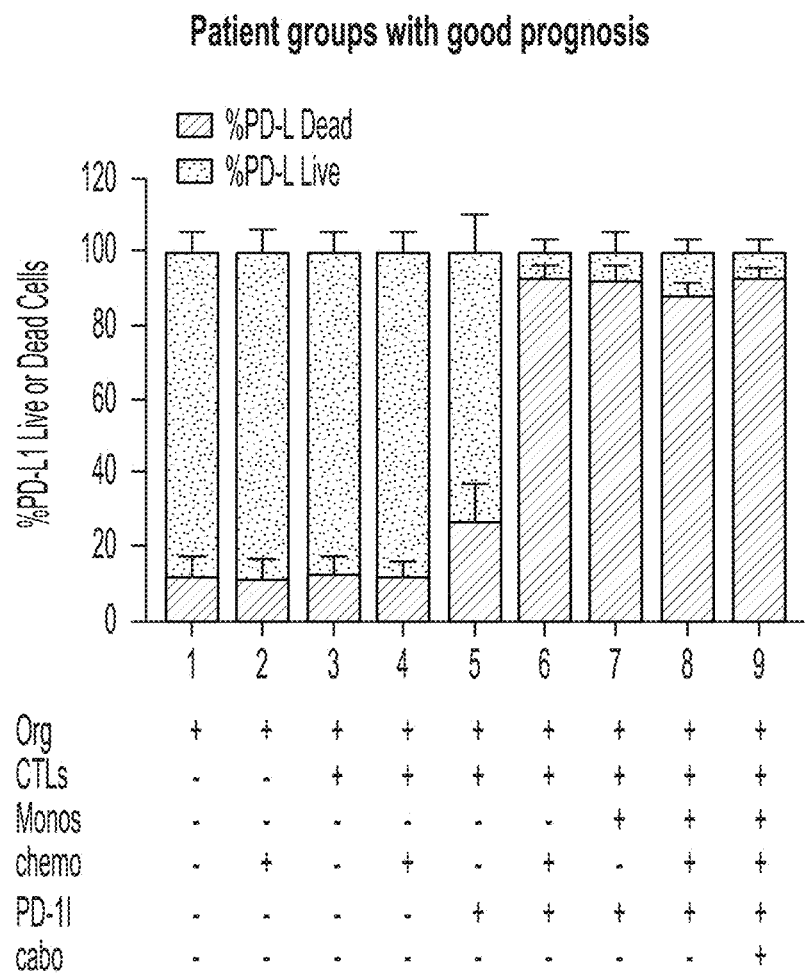
FIGS. 10A-10B. Human-derived autologous pancreatic cancer organoid/immune cell co-cultures. Percent of live/dead PD-L1-expressing organoids in co-cultures derived from (FIG. 10A) patients with a good prognosis, and (FIG. 10B) patients with a high stage or poor prognosis. *P<0.05 compared to condition 1.
Figure 10B:
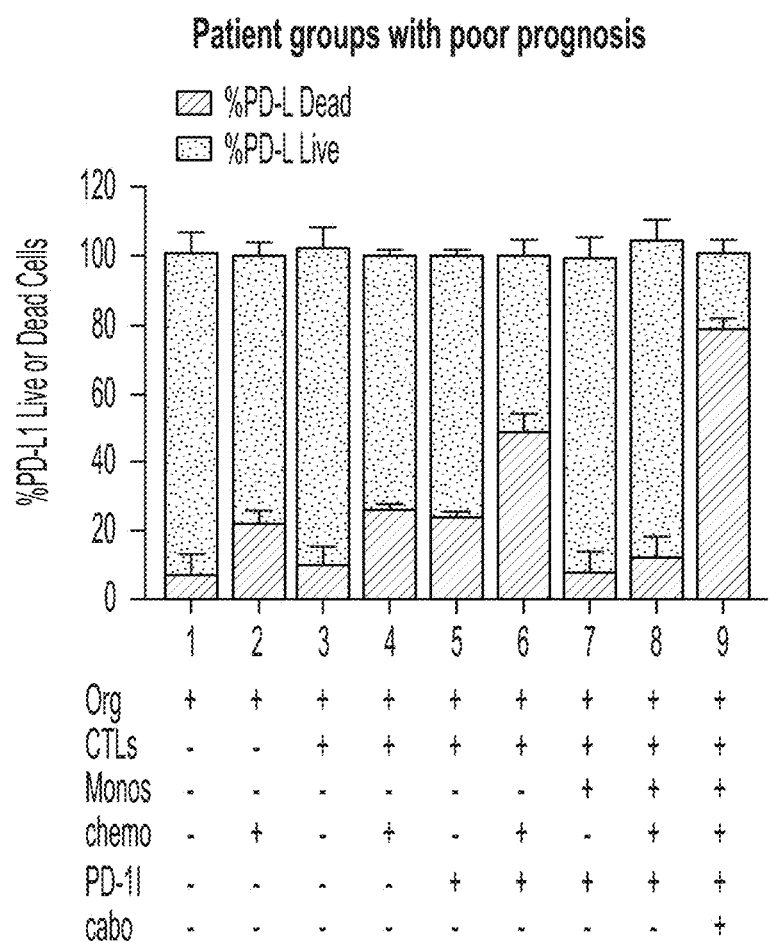
Figure 11A:
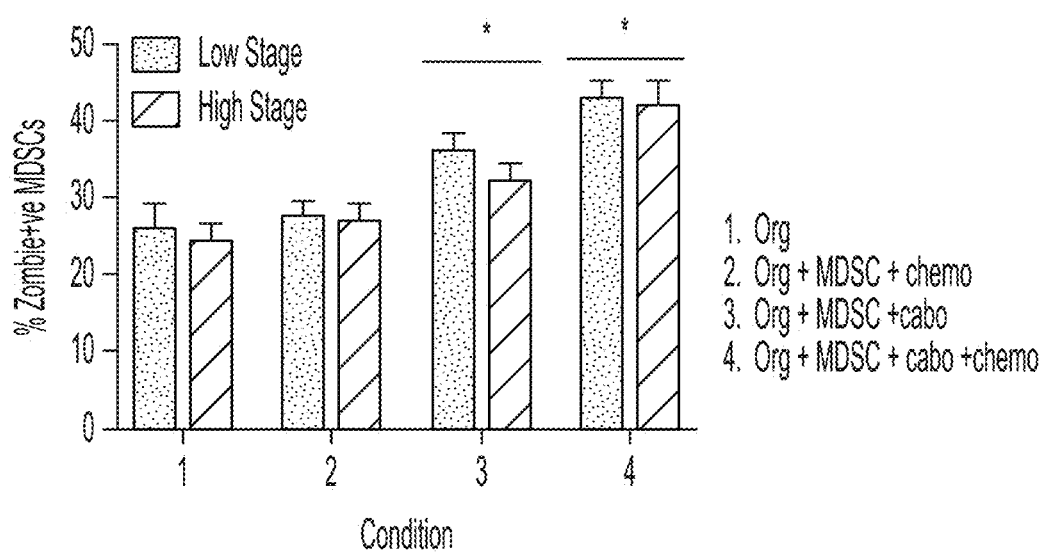
FIGS. 11A-11B. Characterization of co-cultures by flow cytometric analysis.
Figure 11B:
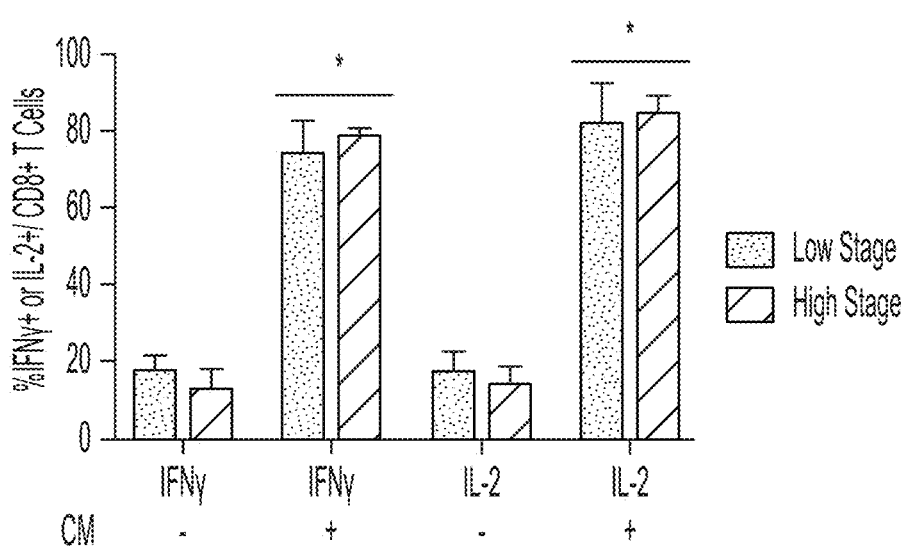

In an autologous organoid/CTL co-culture derived from patients with an early stage tumor, organoids were sensitive to chemotherapy and nivolumab (PD-1Inh) treatment (condition 6, FIG. 7F, 7G), whereby the addition of MDSCs did not affect PD-L1 expressing cell death (condition 8, FIGS. 7F, 7G). In contrast to organoids derived from patients with early stage tumors, an organoid/immune cell co-culture derived from patients with an advanced stage tumors exhibited insignificant organoid cell death when cultures were treated with nivolumab (PD-1Inh) in combination with chemotherapy (condition 6, FIGS. 7F, 7I). Importantly, the inclusion of MDSCs in these co-cultures hindered the efficacy of checkpoint inhibition by nivolumab, resulting in increased PD-L1 expressing cell viability (condition 8, FIGS. 7F, 7I). Depleting the co-culture of MDSCs with the addition of cabozantinib (cabo) maximized the efficacy of checkpoint inhibition and significantly increased PD-L1 expressing cell death (condition 9, FIGS. 7F, 7I). Importantly, PD-L1 expressing cell death in response to combination treatment correlated with significantly increased CTL proliferation (FIGS. 7H, 7J). FIG. 7F is a schematic diagram summarizing the composition and treatments of co-culture conditions 3, 6, 8 and 9. All experimental co-culture conditions are shown in FIGS. 10A-10B. Flow cytometric analysis demonstrated a significant decrease in viable MDSCs in response to cabo treatment within co-cultures (FIG. 11A). Flow cytometric analysis also demonstrated a significant activation of CTLs when co-cultured with autologous dendritic cells that were pulsed with the conditioned media of autologous PDAC patient-derived organoids prior to co-culture with PDAC organoids (FIG. 11B).

Figure 7C:
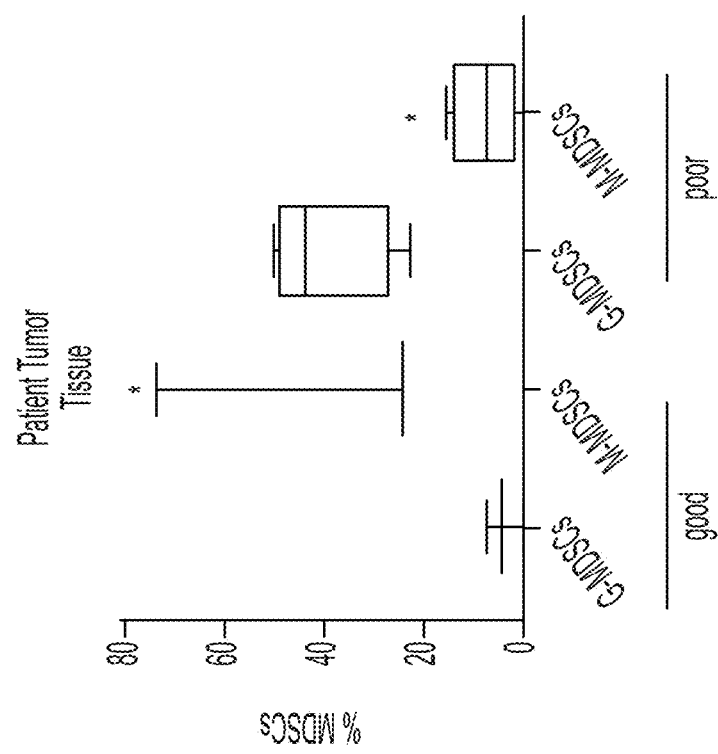

Further, the co-culture of patient-derived organoids with autologous immune cells, in combination with the analysis of infiltrating G-MDSCs, is a more reliable approach for the prediction of disease progression and survival. For example, the PLOT organoid line did not respond well to chemotherapy alone in vitro, and this was reflected by the poor response of the patient to the same therapy (FIGS. 5A, 5B). However, the model predicted that the patient had no recurrence based on few G-MDSCs in the tumor microenvironment, and almost a complete response to the combination of chemotherapy and checkpoint inhibition in vitro (FIGS. 7C, 7G). Consistent with these observations, this patient did not show any sign of recurrent disease 1 year post-surgery. Another patient-derived organoid line, P28T, was predicted to have disease recurrence in the model with significant infiltrating G-MDSCs, and a partial response to the combination of chemotherapy and checkpoint inhibition (FIGS. 7C, 7I). In agreement with the observation made in the P28T organoid/immune cell co-culture, the patient from which these organoid and immune cells were derived showed signs of recurrent disease only 7 months post-surgery. The only measure of patient prognosis that corresponded with the organoid/immune cell co-culture model was patient TMN staging (FIG. 5C). Patient P10T had a stage D3 tumor, whereas patient P28T had a stage III tumor. Thus, organoid/immune cell co-cultures from patients were into advanced and early stage tumors based on their TMN grade.

Autologous organoid-immune cell co-cultures are able to capture the response of tumors to chemotherapeutics, but also reflect the immune cell response to such treatments. This refined approach better represents the tumor microenvironment during time of treatment and overall outcome, not just response to chemotherapeutics. The approach also identifies the role of G-MDSCs in anti-PD1 therapy resistance in the context of PDAC patients within this study.

Figure 12A:
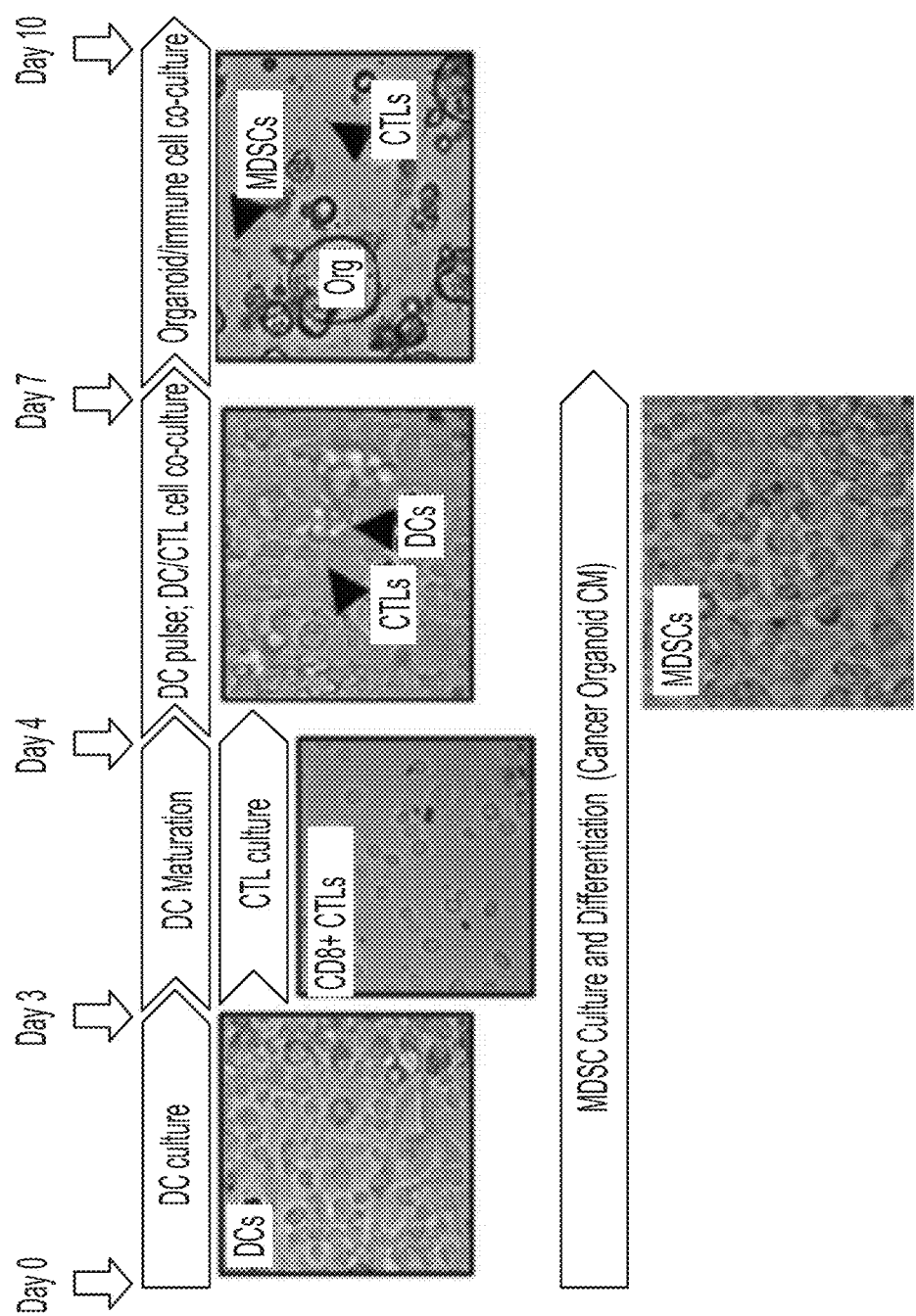
Figure 12B:
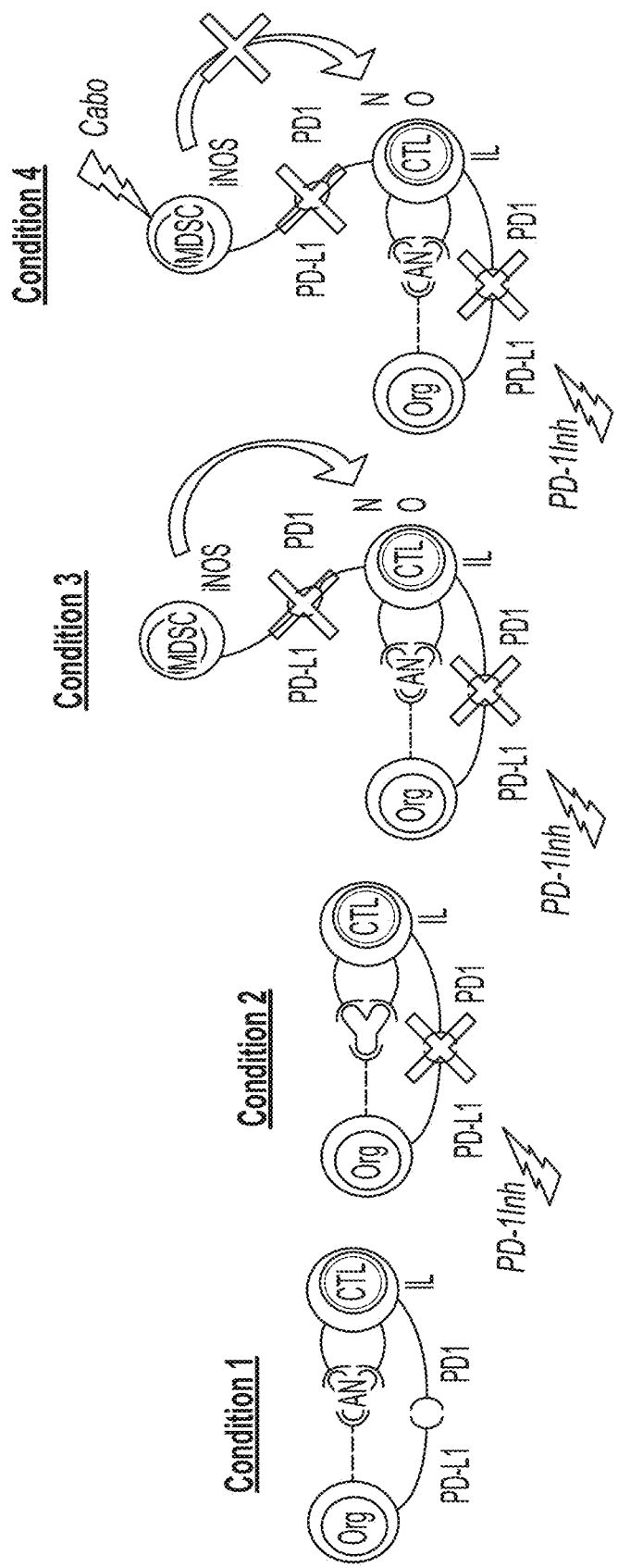

Example 8. MDCSs Disrupt the Efficacy of Checkpoint Inhibition in Mouse-Derived Organoid/Immune Cell Co-Culture To investigate whether MDSCs disrupt the efficacy of checkpoint inhibition in PDAC tumor survival, a pancreatic cancer organoid/CTL/MDSC co-culture was developed. FIG. 12A is an overview of the experimental approach developed by the research team to co-culture pancreatic cancer organoids with autologous immune cells. The protocol is executed and data analyzed within 10 days of the start of organoid and immune cell cultures (FIG. 12A). Importantly, tumor antigen-pulsing of DCs and CTL activation at day 4 of the protocol is particularly useful in developing a system that is closest to physiological relevance. Mice were orthotopically transplanted with syngeneic 7940b pancreatic cancer cells. After 14 days, pancreatic cancer tumors were extracted. Bone marrow and splenocytes were extracted from mice. Monocytes and dendritic cells were derived from bone marrow and CTLs were extracted from splenocytes. Autologous organoid/CTL co-cultures treated with InVivo Plus anti-mouse PD-1 (PD-1Inh) exhibited significant organoid death (condition 2, FIGS. 12B, 12D, 12H) compared to untreated controls (condition 1, FIGS. 12B, C, G). Importantly, when MDSCs were added to the co-culture this response was inhibited (condition 3, FIGS. 12B, 12E, 12F). The addition of cabozantinib (cabo) to the organoid/CTL/MDSC co-culture depleted MDSCs from culture and maximized the efficacy of checkpoint inhibition to induce PD-L1 expressing cancer organoid death (condition 4, FIGS. 12F, 12J). Organoid death was quantified by flow cytometry of Zombie (viability dye)+/EpCAM+/PD-L1+ cells (data not shown).

Figure 12K:
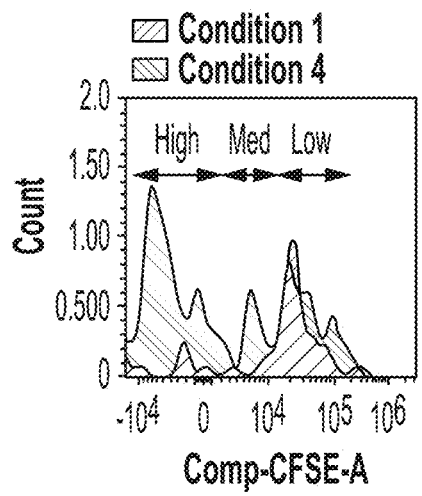
Figure 12L:
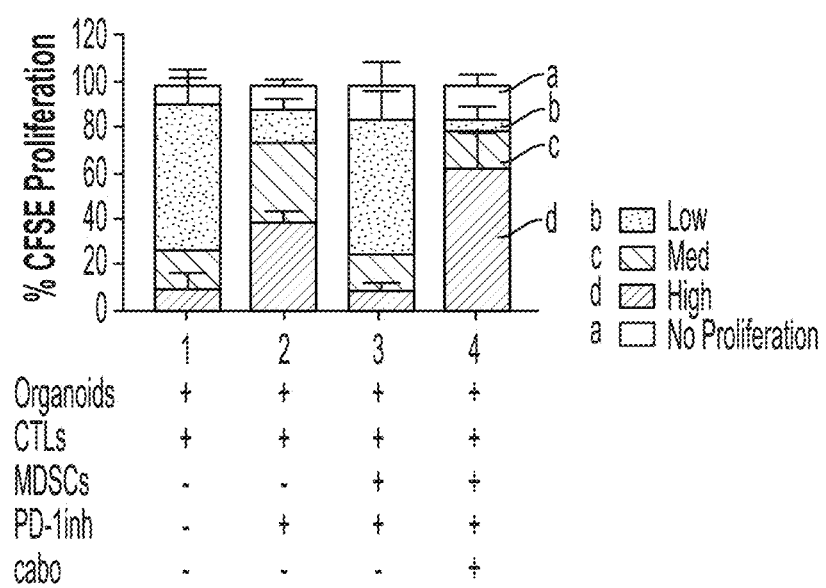

To identify the impact of MDSCs on CD8+ T cell proliferation cell CFSE uptake within the same co-culture was assayed. CD8+ T cells within cultures of pancreatic cancer organoids without autologous MDSCs exhibited an increase in medium CTL proliferation in response to PD-1Inh and chemotherapy (condition 2, FIG. 12L). This proliferative response was diminished with the introduction of MDSCs within the co-culture (condition 3, FIG. 12L). Interestingly, combinatorial treatment with PD-1Inh and cabozantinib resulted in the induction of CD8+ T cell proliferation (condition 4, FIG. 12K, 12L) compared to condition 1 (FIG. 12K, 12L).

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

We claim:

1. A method for preparing an autologous pancreatic tumor organoid and immune cell co-culture that mimics the pancreatic tumor microenvironment, the method comprising:
   (a) culturing pancreatic tumor cells obtained from a patient in culture media to provide a pancreatic tumor organoid and organoid-conditioned media;
   (b) pulsing dendritic cells derived from the patient with a portion of the organoid-conditioned media;
   (c) contacting the pulsed dendritic cells with cytotoxic T lymphocytes (CTLs) obtained from the patient in the organoid-conditioned media to activate the CTLs;
   (d) isolating the activated CTLs; and
   (e) co-culturing the pancreatic tumor organoid with (1) the activated CTLs, and (2) myeloid derived suppressor cells (MDSCs) derived from the patient, to obtain an autologous pancreatic tumor organoid and immune cell co-culture that mimics the pancreatic tumor microenvironment.

2. The method of claim 1, wherein culturing pancreatic tumor cells in the culture media comprises suspending pancreatic tumor cells in a basement membrane matrix and overlaying the culture media.

3. The method of claim 1, wherein co-culturing the pancreatic tumor organoid with the activated CTLs, and the MDSCs comprises suspending the pancreatic tumor organoid, activated CTLs, and MDSCs in a basement membrane matrix and overlaying pancreatic culture media.

4. The method of claim 1, wherein the dendritic cells are matured from peripheral blood mononuclear cells (PBMCs) obtained from the patient.

5. The method of claim 1, wherein the CTLs are extracted from PBMCs obtained from the patient.

6. The method of claim 1, wherein the MDSCs are differentiated from PBMCs obtained from the patient by culturing the PBMCs in a portion of the organoid-conditioned media.

7. The method of claim 6, wherein the MDSCs comprise granulocytic MDSCs (G-MDSCs) and monocytic MDSCs (M-MDSCs).

8. The method of claim 4, wherein the PBMCs are isolated from a whole blood sample obtained from the patient.

9. The method of claim 1, wherein the patient is a human.

10. The method of claim 1, wherein the pancreatic cancer is pancreatic ductal adenocarcinoma.

* * * * *